United States Patent
Newcomb et al.

(10) Patent No.: US 9,307,970 B2
(45) Date of Patent: Apr. 12, 2016

(54) SURGICAL INSTRUMENTS HAVING ERGONOMIC AND VERSATILE HANDLES AND RELATED SYSTEMS AND METHODS

(75) Inventors: William Levin Newcomb, Newport News, VA (US); David Lorin Newcomb, Morrisville, NC (US); Stephen Duane Tester, Cary, NC (US); Emily JoAnne Newcomb, Morrisville, NC (US)

(73) Assignee: Cecore LLC, Morrisville, NC (US)

( * ) Notice: Subject to any disclaimer, the term of this patent is extended or adjusted under 35 U.S.C. 154(b) by 264 days.

(21) Appl. No.: 14/001,420

(22) PCT Filed: Feb. 24, 2012

(86) PCT No.: PCT/US2012/026420
§ 371 (c)(1),
(2), (4) Date: Nov. 6, 2013

(87) PCT Pub. No.: WO2012/161782
PCT Pub. Date: Nov. 29, 2012

(65) Prior Publication Data
US 2014/0051936 A1    Feb. 20, 2014

Related U.S. Application Data

(60) Provisional application No. 61/446,646, filed on Feb. 25, 2011, provisional application No. 61/540,913, filed on Sep. 29, 2011.

(51) Int. Cl.
*A61B 17/02*    (2006.01)
*A61B 17/3201*    (2006.01)
(Continued)

(52) U.S. Cl.
CPC .............. *A61B 17/02* (2013.01); *A61B 17/00* (2013.01); *A61B 17/282* (2013.01);
(Continued)

(58) Field of Classification Search
CPC .............. A61B 17/28; A61B 17/0206; A61B 17/2841; A61B 17/2909; B25B 27/205; B25B 13/12
See application file for complete search history.

(56) References Cited

U.S. PATENT DOCUMENTS 3,398,746 A * 8/1968 Abramson .................... 606/147
4,674,501 A    6/1987 Greenberg
(Continued)

FOREIGN PATENT DOCUMENTS

WO    WO 00/67649 A1    11/2000

OTHER PUBLICATIONS

Extended European Search Report Corresponding to European Application No. EP12789739.5, Date of Mailing: Jul. 4, 2014; 10 pages.
International Preliminary Report on Patentability for PCT/US12/26420 dated Jul. 8, 2013, 15 pages.
International Search Report and Written Opinion for PCT/US026420 dated May 30, 2012, 12 pages.
(Continued)

*Primary Examiner* — Andrew Yang
(74) *Attorney, Agent, or Firm* — Myers Bigel & Sibley, PA

(57) ABSTRACT

A surgical instrument includes first and second members, with each member including a handle adjacent a first end of the member, a working portion having an inner surface and an outer surface and extending from a second, opposite end of the member, and a pivot portion located between the handle and the working portion. The first and second members are pivotally connected at the pivot portions about a pivot axis such that the handles are movable between an open position in which the handles are spaced apart and the working portions are adjacent one another and a closed position in which the handles have been brought together and the working portions are spaced apart.

28 Claims, 15 Drawing Sheets

(51) Int. Cl.
*A61B 17/285* (2006.01)
*B26B 13/12* (2006.01)
*A61B 17/28* (2006.01)
*B25B 27/20* (2006.01)
*A61B 17/29* (2006.01)
*A61B 17/3209* (2006.01)
*A61B 17/00* (2006.01)

(52) U.S. Cl.
CPC .......... *A61B 17/285* (2013.01); *A61B 17/2841* (2013.01); *A61B 17/3201* (2013.01); *A61B 17/0206* (2013.01); *A61B 17/28* (2013.01); *A61B 17/2909* (2013.01); *A61B 17/3209* (2013.01); *A61B 2017/00424* (2013.01); *A61B 2017/2911* (2013.01); *B25B 27/205* (2013.01); *B26B 13/12* (2013.01)

(56) References Cited

U.S. PATENT DOCUMENTS

| | | | |
|---|---|---|---|
| 5,236,436 A | 8/1993 | Koros et al. | |
| 5,458,029 A * | 10/1995 | Walsky | 81/302 |
| 5,522,839 A | 6/1996 | Pilling | |
| 5,930,440 A | 7/1999 | Bar-Or | |
| 6,013,028 A | 1/2000 | Jho et al. | |
| 6,478,028 B1 | 11/2002 | Paolitto et al. | |
| 2001/0021861 A1 | 9/2001 | Boebel et al. | |
| 2002/0169459 A1 | 11/2002 | Porat | |
| 2005/0215864 A1* | 9/2005 | Jang | 600/217 |
| 2006/0287640 A1 | 12/2006 | Perlin | |
| 2011/0034918 A1 | 2/2011 | Reschke | |

* cited by examiner

SURGICAL INSTRUMENTS HAVING ERGONOMIC AND VERSATILE HANDLES AND RELATED SYSTEMS AND METHODS

RELATED APPLICATIONS

This application is a 35 U.S.C. §371 national phase application of PCT International Application No. PCT/US2012/026420, filed Feb. 24, 2012, which claims priority to U.S. Provisional Patent Application No. 61/446,646, filed Feb. 25, 2011 and to U.S. Provisional Patent Application No. 61/540,913, filed Sep. 29, 2011, the disclosures of which are incorporated by reference herein in their entireties. The above PCT International Application was published in the English language and has International Publication No. WO 2012/161782 A1.

FIELD OF THE INVENTION

This invention relates to instruments and tools, such as surgical instruments, and handles associated therewith.

BACKGROUND

Handles for instruments and tools dictate how the instrument or tool will be grasped and manipulated by a user. A simple example is a pair of scissors. A common pair of scissors includes a first handle having a generally circular opening and a second handle having an elongated opening. The circular opening is designed to receive the operator's thumb and the elongated opening is designed to receive two or more fingers. Due to the asymmetrical design, these types of scissors are not reversible and often require reorientation when grabbed.

Some instruments and tools (including scissors) do include handles that are symmetrical. For example, a common hemostat includes a pair of handles, with each handle having a generally circular opening. However, such a configuration may not be suitable for users of varying hand sizes and/or may not allow for adequate control during use.

In the field of minimally invasive surgery, such as laparoscopy, tools that perform functions such as enlarging openings, grasping organs and the like generally include handles that suffer from the above-described drawbacks. For example, common hemostats and forceps are limited in the manner they can be grasped and manipulated and may not be suitable for a range of hand sizes due to the handle design. Also, some of these instruments do not have substantially identical or symmetrical handles and require reorientation when blindly grasped by a busy surgeon. Moreover, the tools are often not only limited by the design of the handles, but also by the limited functionality of the working ends opposite the handles. For example, separate, specialized tools are generally needed to perform the operations of blunt dissection, enlarging openings and/or grasping objects.

SUMMARY

Some embodiments of the invention are directed to a surgical instrument. The surgical instrument includes first and second members. Each member includes a handle adjacent a first end of the member, a working portion having an inner surface and an outer surface and extending from a second, opposite end of the member, and a pivot portion located between the handle and the working portion. The first and second members are pivotally connected at the pivot portions about a pivot axis such that the handles are movable between an open position in which the handles are spaced apart and the working portions are adjacent one another and a closed position in which the handles have been brought together and the working portions are spaced apart.

At least a portion of each working portion outer surface may include an outwardly tapering wedge. Each working portion may include an outwardly extending lip at the second end of the first and second members. Each working portion may include an outwardly extending lip adjacent the wedge, wherein the wedge and the lip define a valley therebetween on the working portion outer surface. Each working portion may include a tapered portion that tapers inwardly from the lip to the second end of a respective first and second member. The second end of each of the first and second members may be shaped such that, when the handles are in the open position, the adjacent second ends of the first and second members define a blunt tip. The second end of the first and second members may be flat or rounded. At least a portion of each working portion inner surface may include a plurality of teeth.

According to some embodiments, the surgical instrument includes a biasing member configured to bias the handles toward the open position. The biasing member may be positioned between the handles.

The handles may be symmetrical or substantially symmetrical about an axis that is normal to the pivot axis and extends between the working portions. The handles may be identical or substantially identical.

According to some embodiments, the handle of each member includes at least one opening defined by an inner wall, an outer wall, a first end wall at the first end of the member and a second end wall located adjacent or proximate the pivot portion of the member. The handle of each member may include a first opening defined by the inner wall, the outer wall, the first end wall, and an interior wall and a second opening defined by the inner wall, the outer wall, the second end wall, and the interior wall, wherein the first opening is elongated and the second opening is generally elliptical or oval and separated from the first opening by the interior wall.

According to some embodiments, the handle of each member includes: a first elongated opening defined by the inner wall, the outer wall, the first end wall, and a first interior wall; a second generally elliptical or oval opening defined by the inner wall, the outer wall, the second end wall, and a second interior wall; and a third generally elliptical or oval opening defined by the inner wall, the outer wall, and the first and second interior walls, the third opening located between the first and second openings of the handle. The third opening may be elongated relative to the second opening and oriented at an oblique angle relative to a major axis of the second opening. The first opening of each handle may be contoured such that the first interior wall has a first rounded portion adjacent the inner wall and a second rounded portion adjacent the outer wall, with the first and second rounded portions separated by relatively raised center portion.

Other embodiments of the invention are directed to a handle system for use with a tool. The handle system includes first and second elongated handles, with each handle extending from a first end to a second opposite end. Each handle includes an inner wall, an outer wall, a first end wall at the first end of the handle and extending between the inner wall and the outer wall, and a second end wall located proximate the second end of the handle and extending between the inner wall and the outer wall. The handles are pivotally connected at the handle second ends such that the handles are pivotable between an open position wherein the inner walls are spaced apart and a closed position wherein the inner walls are adjacent one another. Each handle also includes: a first elongated opening defined by the first end wall, the inner wall, the outer wall and an interior wall located between the first and second end walls and extending between the inner and outer walls; and a second generally elliptical or oval opening defined by the second end wall, the inner wall, the outer wall and the interior wall.

Each handle may include first and second interior walls that each extend between the inner and outer walls and a third generally elliptical or oval opening, wherein: the first elongated opening is defined by the first end wall, the inner wall, the outer wall and first interior wall; the second generally elliptical or oval opening is defined by the second end wall, the inner wall, the outer wall and the second interior wall; and the third generally elliptical or oval opening is located between the first and second openings and is defined by the inner wall, the outer wall, and the first and second interior walls. The third opening may be elongated relative to the second opening and oriented at an oblique angle relative to a major axis of the second opening. The first opening of each handle may be contoured such that the first interior wall has a first rounded portion adjacent the inner wall and a second rounded portion adjacent the outer wall, with the first and second rounded portions separated by relatively raised center portion.

Other embodiments of the invention are directed to a handle system for use with a tool. The handle system includes first and second elongated handles, with each handle extending from a first end to a second opposite end adapted to receive a working end portion. The handles are pivotally connected proximate their second ends and are pivotable about a pivot axis. Each handle includes an inner wall, an outer wall, a first end wall located at the first end of the handle and extending between the inner and the outer wall, a first interior wall located closer to the second end of the handle than the first end wall and extending between the inner and the outer wall, a second interior wall located closer to the second end of the handle than the first interior wall and extending between the inner and the outer wall, and a second end wall located closer to the second end of the handle than the second interior wall and extending between the inner and the outer wall. Each handle also includes: a first elongated opening defined by the first end wall, the inner wall, the outer wall and the first interior wall; a second generally elliptical opening defined by the second end wall, the inner wall, the outer wall and the second interior wall; and a third generally elliptical opening located between the first and second openings and defined by the inner wall, the outer wall, and the first and second interior walls.

The third opening may be elongated relative to the second opening and oriented at an oblique angle relative to a major axis of the second opening. The first opening of each handle may contoured such that an inner surface of the first interior wall has a first rounded portion adjacent the inner wall and a second rounded portion adjacent the outer wall, with the first and second rounded portions separated by relatively raised center portion of the inner surface of the first interior wall.

According to some embodiments, each handle outer wall is contoured such that an outer surface of the outer wall includes a valley. According to some embodiments, the first and second handles are substantially symmetrical about an axis that is normal to the pivot axis and extends between the handles.

The handle system may be in combination with a pair of working end portions. One each of the working end portions extends from a respective second end of the first and second handles. The handles may be configured such that as the handles are moved apart the working portions move apart and as the handles are brought together the working portions come together. Alternatively, the handles may be configured such that as the handles are moved apart the working portions come together and as the handles are brought together the working portions move apart.

Other embodiments of the invention are directed to a method of performing laparoscopic surgery. The method includes providing a tool having first and second pivotally connected elongated members, with each member including a handle extending from a first end of the member and a working portion extending from a second, opposite end of the member, wherein the handles are movable between an open position in which the working portions are adjacent one another to a closed position in which the handles have been brought together and the working portions have moved apart. The method further includes the steps of: with the handles in the open position, inserting the working portions in an opening in an abdominal wall; then moving the handles toward the closed position; then moving the handles toward the open position; and then withdrawing the working portions from the opening in the abdominal wall According to some embodiments, the method further includes the step of enlarging the opening of the abdominal wall with the working portions during the step of moving the handles toward the closed position. According to some embodiments, the method further includes the step of grasping an organ for extraction with the working portions during the step of moving the handles toward the open position, wherein the step of withdrawing the working portions from the opening comprises withdrawing the working portions and the grasped object from the opening. According to some embodiments, the method includes: enlarging the opening of the abdominal wall with the working portions during the step of moving the handles toward the closed position; and grasping an organ for extraction with the working portions during the step of moving the handles toward the open position; wherein the step of withdrawing the working portions from the opening comprises withdrawing the working portions and the grasped object from the enlarged opening.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

DETAILED DESCRIPTION OF EMBODIMENTS OF THE INVENTION

Figure 1:
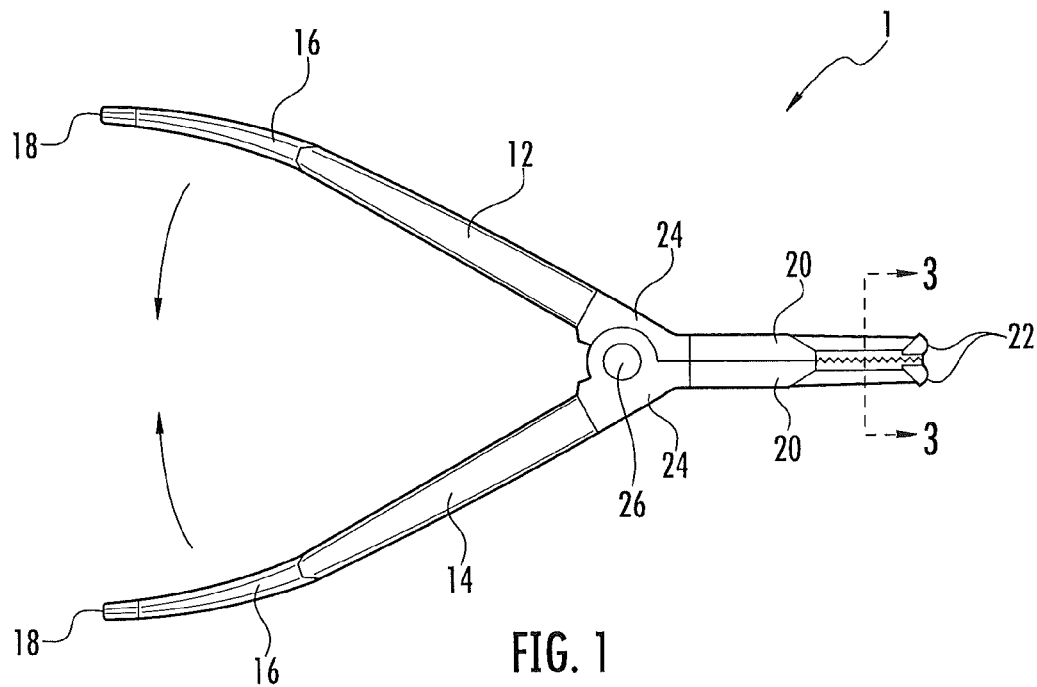
FIG. 1 is a side view of a surgical instrument in a first position according to some embodiments.

The present invention now will be described more fully with reference to the accompanying drawings, in which embodiments of the invention are shown. However, this invention should not be construed as limited to the embodiments set forth herein. Rather, these embodiments are provided so that this disclosure will be thorough and complete, and will fully convey the scope of the invention to those skilled in the art. In the drawings, like numbers refer to like elements throughout. Thicknesses and dimensions of some components may be exaggerated for clarity.

As used herein, the term "comprising" or "comprises" is open-ended, and includes one or more stated features, integers, elements, steps, components or functions but does not preclude the presence or addition of one or more other features, integers, elements, steps, components, functions or groups thereof. As used herein, the term "and/or" includes any and all combinations of one or more of the associated listed items.

As used herein, the common abbreviation "e.g.," which derives from the Latin phrase "exempli gratia," may be used to introduce or specify a general example or examples of a previously mentioned item, and is not intended to be limiting of such item. If used herein, the common abbreviation "i.e.," which derives from the Latin phrase "id est," may be used to specify a particular item from a more general recitation.

The terminology used herein is for the purpose of describing particular embodiments only and is not intended to be limiting of the invention. As used herein, the singular forms "a," "an" and "the" are intended to include the plural forms as well, unless the context clearly indicates otherwise.

Well-known functions or constructions may not be described in detail for brevity and/or clarity.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In addition, spatially relative terms, such as "under," "below," "lower," "over," "upper," "downward," "upward," "inward, "outward" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

It will be understood that when an element is referred to as being "coupled" or "connected" to another element, it can be directly coupled or connected to the other element or intervening elements may also be present. In contrast, when an element is referred to as being "directly coupled" or "directly connected" to another element, there are no intervening elements present.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Figure 2:
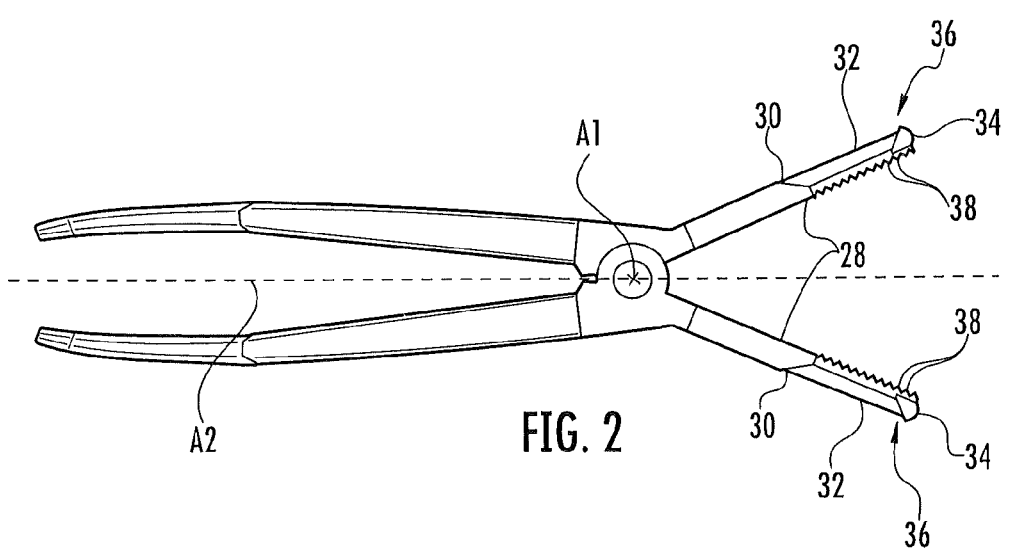
FIG. 2 is a side view of the surgical instrument of FIG. 1 in a second position according to some embodiments.

A surgical instrument 1 according to some embodiments is illustrated in FIGS. 1 and 2. The surgical instrument 1 includes first and second members 12, 14 that are pivotally connected. Each of the first and second members 12, 14 includes a handle 16 that is adjacent to a first end 18 of the member. Each of the first and second members 12, 14 includes a working portion 20 that extends from a second end 22 that is opposite the first end 18 of the member.

Each of the first and second members 12, 14 also includes a pivot portion 24 that is positioned between the handle 16 and the working portion 20 of the member. In some embodiments, the handle 16 of each member 12, 14 extends between the first end 16 and the pivot portion 24 of the member and/or the working portion 20 of each member 12; 14 extends between the second end 22 and the pivot portion 24 of the member.

The first and second members 12, 14 are pivotally connected at their respective pivot portions 24. A pivot member 26 connects the first and second members 12, 14 and allows them to pivot about a pivot axis A1 defined by the pivot member 26. The pivot portions 24 may overlap one another or may be interleaved in various embodiments. The pivot member 26 may penetrate at least a portion of each of the pivot portions 24. The pivot member 26 may take a variety of forms, such as a pin, post, screw or the like.

The first and second members 12, 14 are pivotally connected such that the handles 16 are movable between a first or open position (FIG. 1) and a second or closed position (FIG. 2). In the first position, the handles 16 are spaced apart and the working portions 20 are adjacent one another. In some embodiments, and as illustrated, at least a portion of inner surfaces (described below) of the working portions 20 are in contact with each other with the handles 16 in the first position. In the second position, the handles 16 have been brought together (in the direction shown by the arrows in FIG. 1) and the working portions 20 are spaced apart. Put another way, the instrument in the illustrated embodiment has a "reverse scissors action" such that as the handles 16 close, the working portions 20 open and vice-versa. In some other embodiments, the instrument may have a scissors-like action such that handles 16 and working portions 20 open and close together.

As illustrated, the first and second members 12, 14 are identical or substantially identical. The first and second members 12, 14 may be symmetrical or substantially symmetrical relative to an axis A2 that is normal to the pivot axis A1 and passes between the handles 16 and/or the working portions 20.

The substantially identical or symmetrical nature of the first and second members 12, 14 can provide certain advantages. For example, the instrument is reversible (i.e., can be used with equal effectiveness in the user's left or right hand). This can ensure that the instrument is ready to use and does not require substantial reorientation when grabbed blindly, such as by a busy surgeon. Moreover, the substantially identical or symmetrical members 12, 14 may provide for simpler manufacturing and assembly and reduced costs associated therewith. It is contemplated that, in some embodiments, the pivot portions 24 may not be completely identical to facilitate certain pivot members 26 or other pivot arrangements. It is also contemplated that, in some embodiments, the working portions 20 may be slightly different, as described in more detail below.

Each of the first and second members 12, 14 may be monolithic. For example, the handle 16, the working portion 20 and the pivot portion 24 may be integrated. In other embodiments, at least one of the handle 16, working portion 20, and pivot portion 24 of each of the first and second members 12, 14 may be a separate component and attached or connected to the remainder of the components. For example, the handle 16 and the pivot portion 24 may be integrated and the working portion 20 may be a separate component. In this regard, various working portions may be attachable or connectable to the integrated handle/pivot portion to allow for a modular arrangement such that various operations or procedures may be performed based on the particular working portion selected and attached/connected.

Figure 3A:
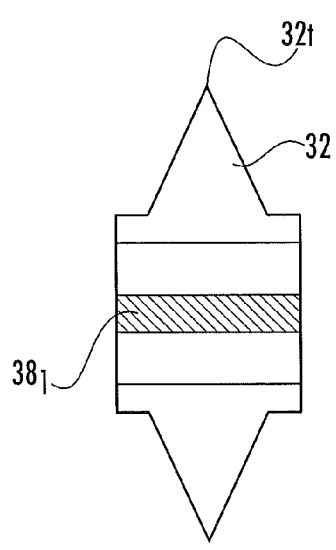
FIGS. 3A and 3B are schematic cross sectional views of a portion of the surgical instrument of FIG. 1 according to some embodiments.
Figure 3B:
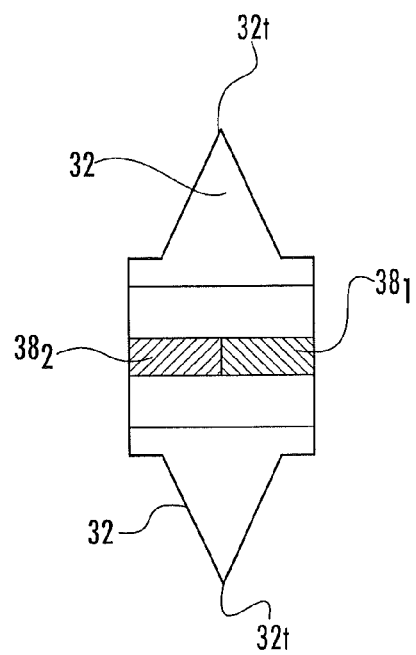

As illustrated in FIG. 2, each of the working portions 20 includes an inner surface 28 and an outer surface 30. At least a portion of each working portion outer surface 30 includes an outwardly tapering wedge 32. As shown in the cross-sectional views of FIGS. 3A and 3B, each wedge 32 may be substantially triangular in shape and may include a relatively sharp or blunt tip 32t.

In the embodiment illustrated in FIGS. 1 and 2, each working portion 20 also includes an outwardly extending lip 34 at the second end 22 of the member. That is, at least a portion of the lip 34 extends outwardly away from the working portion 20 a greater distance than does the wedge 32. Each wedge 32 and lip 34 defines a valley 36 therebetween on the working portion outer surface 30.

As illustrated in FIG. 2, at least a portion of each working portion inner surface 28 includes a plurality of teeth 38. Various configurations of the teeth 38 are contemplated. The teeth 38 associated with each of the working portions 20 may extend along the entire width or substantially the entire width of the inner surface 28. In this sense, the teeth 38 associated with the first member 12 may be offset with respect to the teeth 38 associated with the second member 14. Thus, in the cross-sectional view of FIG. 3A, only tooth $38_1$ associated with one of the members 12, 14 is visible. This is one example in which the working portions 20 may not be precisely identical or symmetrical. In other embodiments, the teeth 38 associated each of the first and second members 12, 14 are configured such that one tooth 38 extends across about one-half the width of the inner surface 28 and another, offset tooth 38 extends across about the other one-half of the width of the inner surface 28. The teeth 38 continue this staggered relationship along a portion of the length of the inner surface 28. This configuration is illustrated in the cross-sectional view of FIG. 3B, in which tooth $38_1$ associated with one of the members 12, 14 and tooth $38_2$ associated with the other of the members 12, 14 is visible. Regardless of the configuration, the teeth 38 are generally arranged such that the working portions 20 can mate or mesh when brought together.

Figure 4:
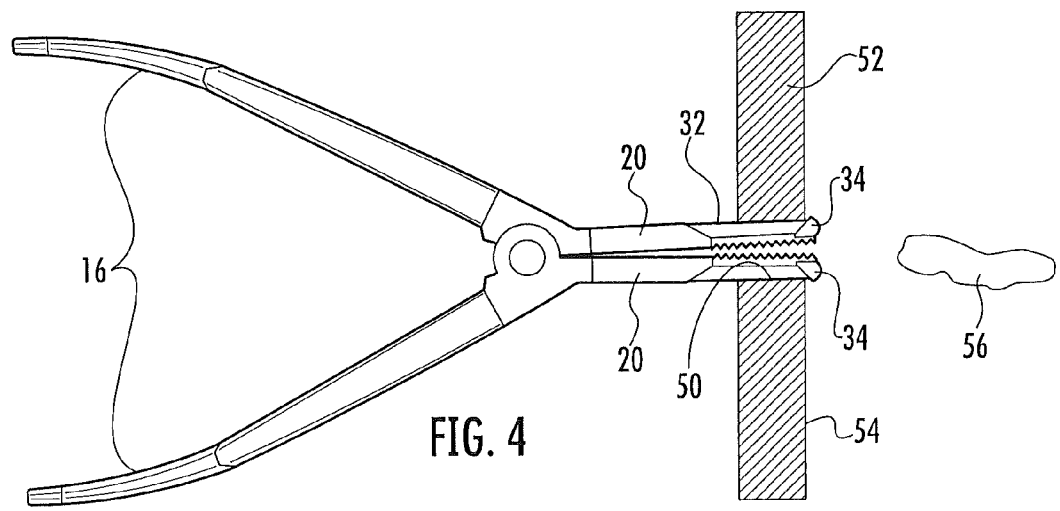
FIG. 4 is a schematic illustration of the surgical instrument of FIG. 1 performing various operations according to some embodiments.

The instrument 1 illustrated in FIGS. 1 and 2 may be particularly useful in minimally invasive surgery such as laparoscopic surgery. Referring to FIG. 4, a user holding the instrument with the handles 16 in the first position (FIG. 1) may insert the working portions 20 into an opening such as a trochar site opening 50 that has been formed in an abdominal wall 52. The handles 16 may be closed or moved toward the second position (FIG. 2) such that the working portions 20 are spread apart to enlarge the opening 50 in the abdominal wall 52. The "reverse-scissor" action of the instrument may allow the user to enlarge the opening with less applied force to the handles and greater precision than with conventional instruments. Moreover, the wedges 32 and the tips 32t associated therewith can allow the user to more easily enlarge the opening 50. That is, the wedges 32 are configured to break, rip or tear through fat, muscle and/or tissue associated with the abdominal wall 52 to enlarge the opening 50. Other tough obstacles may be encountered, such as chronically hardened facial edges of an umbilical hernia defect through which a trochar may be placed during laparoscopic surgery, and the wedges 32 may allow the user to more easily break through such obstacles.

The lips 34 and/or the valleys 36 may provide a locating feature after the working portions 20 are inserted into an opening. For example, referring to FIG. 4, as the handles 16 begin to close and the working portions 20 begin to open, the lips 34 and/or the valleys 36 may be used to catch or hook on an inside surface 54 of the abdominal wall 52. Thus, the lips 34 and/or the valleys 36 may be used to localize the working portions 20 by providing tactile feedback to the user prior to bluntly enlarging the opening 50 in the abdominal wall 52. The lips 34 and/or the valleys 36 may also help prevent the working portions 20 from slipping or popping out during enlargement of the opening 50.

The teeth 38 are configured to grasp an object 56 for extraction without slipping. The object 56 may be any solid organ or portion thereof that is to be extracted from an opening in the abdomen or chest and/or requires widening of an opening in the abdomen or chest prior to extraction (e.g., appendix, gallbladder, ovary, spleen, liver, stomach, small bowel, lung, colon, or a tumor associated with such an organ, or a surgical bag containing such an organ). That is, the handles 16 may be moved apart to thereby close the working portions 20 and grip an organ with the teeth 38 with enough force to remove the organ from the enlarged opening 50 shown in FIG. 4.

Thus, it can be appreciated that the instrument may function to both enlarge a defect or opening in an abdominal wall and grasp an organ for extraction. The enlarging and grasping actions may be used in sequence, thus allowing the two procedures to be accomplished with increased efficiency and with a single instrument, thereby decreasing operating time and improving patient safety.

Furthermore, the handles 16 may be sized with sufficient length and/or surface area to allow the surgeon to apply a significant amount of force to enlarge the opening. In various embodiments, the handles may have an arc length of between about 3 and about 12 inches, between about 4 and about 10 inches, and between about 4 and about 6 inches. Each of the handles may be contoured such that they are adapted to comfortably receive the surgeon's hand when applying force. For example, referring to FIGS. 1 and 2, at least a major portion of a length of the handle 16 of each member 12, 14 may be contoured inwardly from the first end 18 to the pivot portion 24 of the member. Further, the handles 16 may have a smooth outer surface to provide comfort while applying force thereto. This may eliminate lacerations and other injuries that surgeons may encounter when using instruments such as hemostats in blunt dissection of abdominal walls, for example.

The handles 16 are configured for one-hand operation. For example, the user may position a thumb on the outer surface of one of the handles 16 and one or more fingers on the outer surface of the other of the handles 16. As described above, the handles are substantially identical or symmetrical, and therefore are reversible and do not require substantial reorientation even when grabbed blindly.

Other surgical instruments that can perform similar functions but with different handle configurations will now be described. The different handle designs may provide for additional comfort, control and/or versatility.

Figure 5:
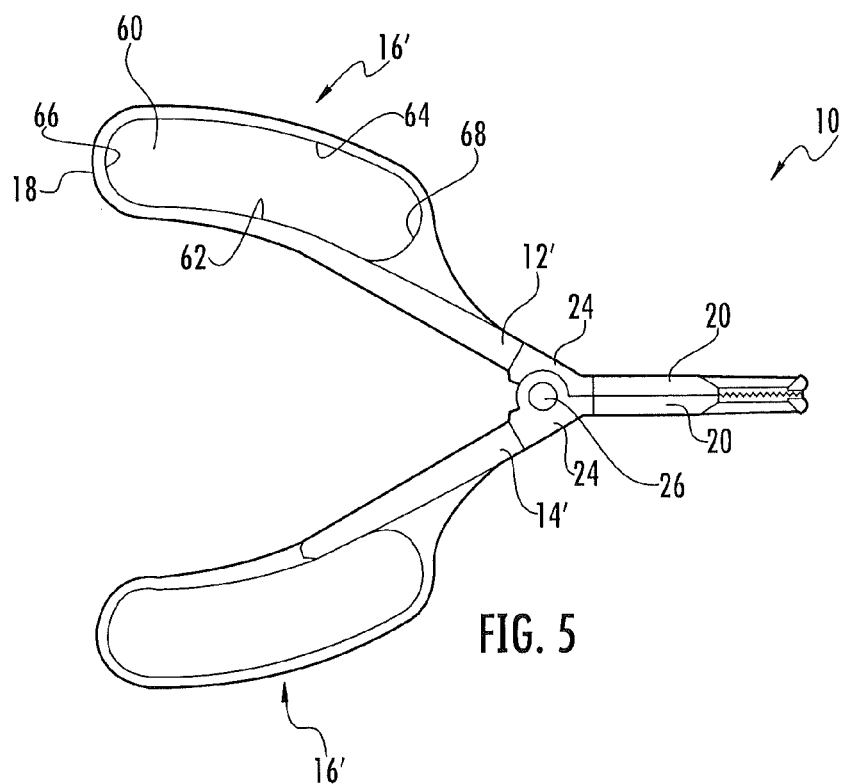
FIG. 5 is a side view of a surgical instrument according to some other embodiments.

A surgical instrument 10 according to some other embodiments is illustrated in FIG. 5. The instrument 10 includes first and second pivotally connected members 12', 14'. Each member 12', 14' includes a working portion 20 and a pivot portion 24 and the members 12', 14' are pivotally connected at a pivot member 26 as described above in connection with the instrument 1. The instrument 10 differs from the instrument 1 in the configuration of the handle 16' associated with each member 12', 14'.

In particular, each handle 16' is "looped" and includes an opening 60 defined by an inner wall 62, an outer wall 64, a first end wall 66 at the first end 18 of the member, and a second end wall 68. The second end wall 68 is positioned closer to the pivot portion 24 than the first end wall 66 and, in some embodiments, the second end wall 68 is positioned adjacent the pivot portion 24.

The handles 16' are substantially identical and therefore the instrument 100 is reversible and does not require reorientation when grabbed blindly. The instrument 100 is configured for one-hand operation with the opening 60 of one of the handles 16' configured to receive a thumb of a user and the opening 60 of the other of the handles 16' configured to receive at least one finger or a plurality of fingers of the user. Thus, the instrument 10 including the openings 60 may further facilitate one-handed operation and may allow more precise control when opening and closing the working portions 20.

The user may apply force against inner surfaces of the inner walls 62 of the handles 14' to close the handles 14'. The user may also apply force against inner surfaces of the outer walls 64 to open the handles. Further, as illustrated, the inner surfaces of the first and second end walls 66, 68 may be contoured such that the user may wedge his or her thumb and/or fingers against these surfaces for additional control during operation. The inner surfaces of the walls defining the inner openings 60 are smooth to prevent abrasions or other injury during use.

The walls defining the openings 60 may help prevent the user's thumb and/or fingers from slipping out during operation. It is also noted that the outer surfaces of the outer walls 66 are contoured and smooth and configured to receive one or more fingers of the user's hand to provide additional versatility.

Figure 6:
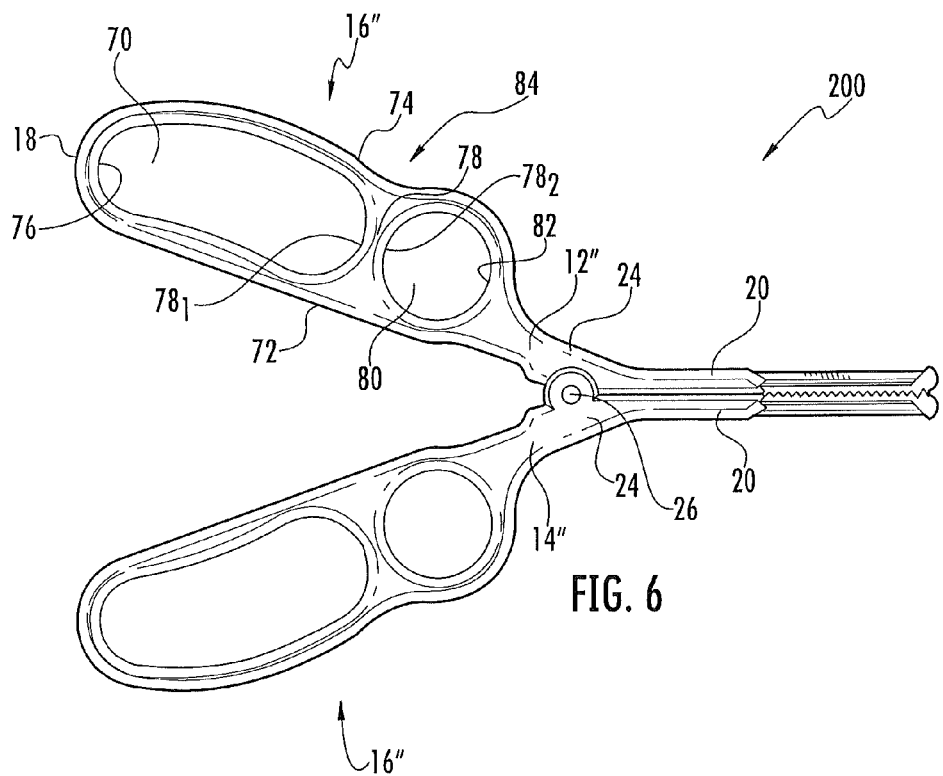
FIG. 6 is a side view of a surgical instrument according to some other embodiments.

A surgical instrument 200 according to some other embodiments is illustrated in FIG. 6. The instrument 200 includes first and second pivotally connected members 12", 14". Each member 12", 14" includes a working portion 20 and a pivot portion 24 and the members 12", 14" are pivotally connected at a pivot member 26 as described above in connection with the instrument 1. The instrument 200 differs from the instruments 1 and 10 in the configuration of the handle 16" associated with each member 12", 14".

Each handle 16" includes a first opening 70 defined by an inner wall 72, an outer wall 74, a first end wall 76 at the first end 18 of the member, and an interior wall 78. Each handle 16" also includes a second opening defined by the inner wall 72, the outer wall 74, a second end wall 82, and the interior wall 78. The second end wall 82 is positioned closer to the pivot portion 24 than is the first end wall 76 and, in some embodiments, is positioned adjacent the pivot portion 24.

In the illustrated embodiment, the first opening 70 is elongated and the second opening 80 is substantially circular in shape. It is contemplated that the second opening 80 may also be elliptical or oval in shape. The first opening 70 is separated from the second opening 80 by the interior wall 78.

The handles 16" are substantially identical and therefore the instrument 200 is reversible and does not require substantial reorientation when grabbed blindly. The instrument 200 is configured for one-handed operation such that a user's thumb can be received in either the first opening 70 or the second opening 80 of one of the handles 16" and at least one of the user's fingers can be received in the first opening 70 and/or the second opening 80 of the other one of the handles 16". The user can urge his or her thumb and fingers against the inner surfaces of the walls defining the openings 70, 80 for control during use. The inner surfaces of the walls defining the openings 70, 80 are smooth to prevent abrasions or other injury during use.

It will be appreciated that the instrument 200 can be held and operated in a variety of ways to provide control as well as accommodate different user preferences and hand sizes. In one exemplary configuration, the user's thumb may be received in either the first opening 70 or the second opening 80 of one of the handles 16" and the in the other of the handles 16" the user's forefinger may be received in the second opening 80 and the user's middle finger and ring finger may be received in the first opening 70.

The walls defining the openings 70, 80 may prevent the user's thumb and fingers from slipping out during operation. In addition, at least a portion of the interior wall 78 may serve a "control point" for the user's fingers in the adjacent openings 70, 80 during manipulation of the instrument 200. For example, when the instrument is grasped in the above-described manner, the user may urge his or her middle finger against a first inner surface $78_1$ of the interior wall 78 and/or may urge his or her forefinger against a second inner surface $78_2$ of the interior wall 78 to provide greater control.

The outer surfaces of each of the outer walls 74 are smooth and may also receive a thumb or one or more fingers of the user. A user may find that placing his or her thumb or at least one finger on one or both of these outer surfaces may allow for greater leverage when closing the handles, for example. In the illustrated embodiment, the outer surfaces of the outer walls 74 includes a valley 84 located between the first and second openings 70, 80. The valley 84 may be configured to receive at least one thumb or finger.

Thus, it will be appreciated that the openings 70, 80 of the handles 16″ allow users to grasp the instrument 200 in a variety of ways to provide the desired comfort and controllability and/or to provide the leverage needed in a particular application. Thumbs and fingers of varying sizes may be placed in any opening 70, 80 or even on the outer surface of the outer wall 74.

Figure 7:
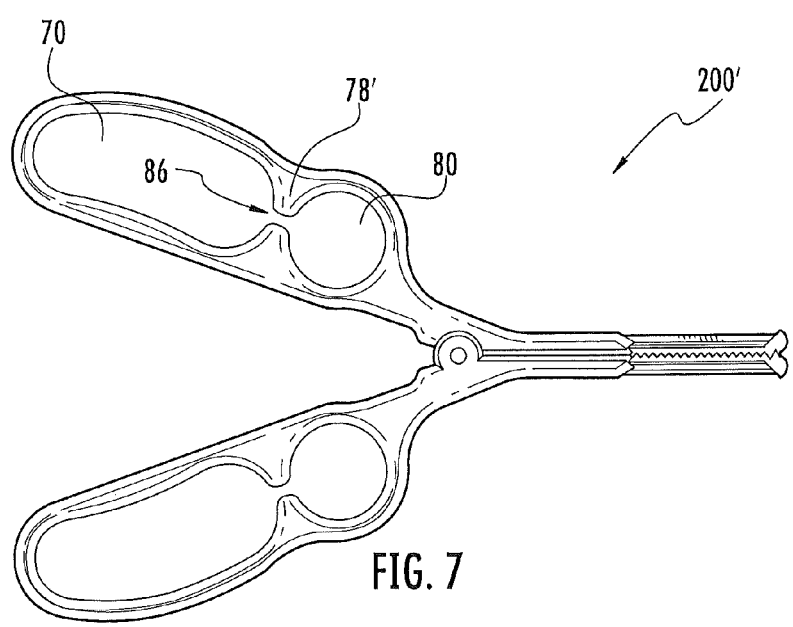
FIG. 7 is a side view of a surgical instrument according to some other embodiments.

The instrument 200′ illustrated in FIG. 7 is substantially identical to the instrument 200 of FIG. 6 with the exception of the interior wall. In the embodiment shown in FIG. 7, the interior wall 78′ includes a gap 86 between the first and second openings 70, 80. The gap 86 reduces the material used and may provide manufacturing advantages.

Figure 8:
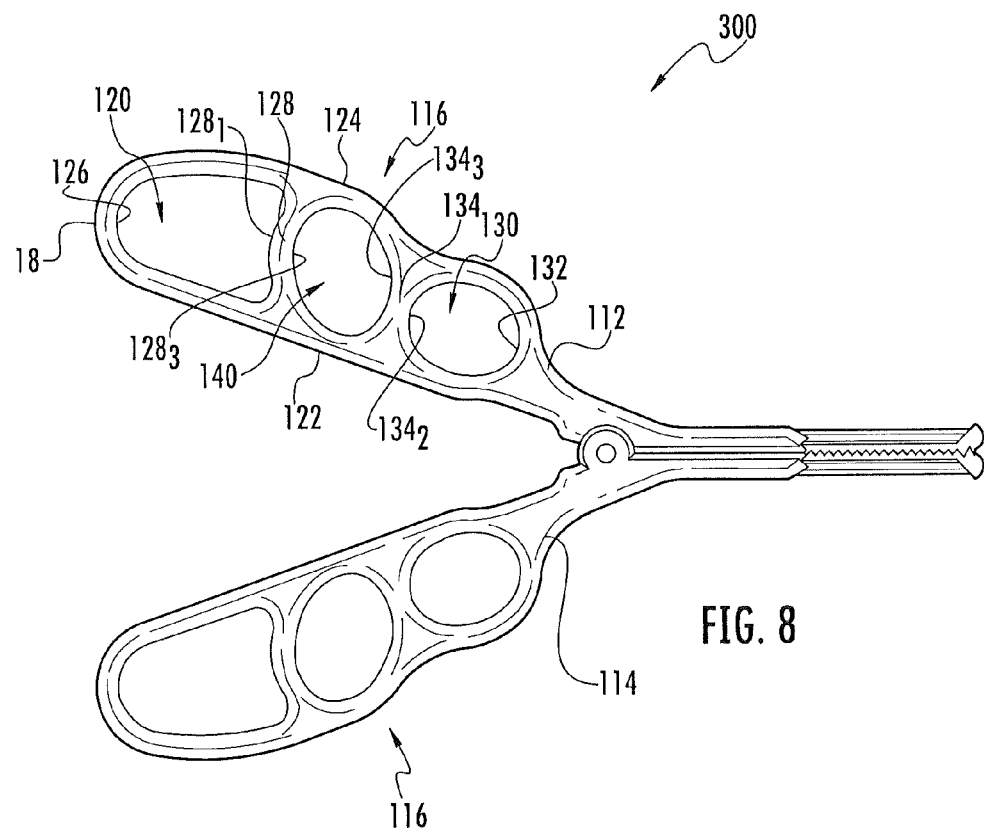
FIG. 8 is a side view of a surgical instrument in a first position according to some embodiments.
Figure 9:
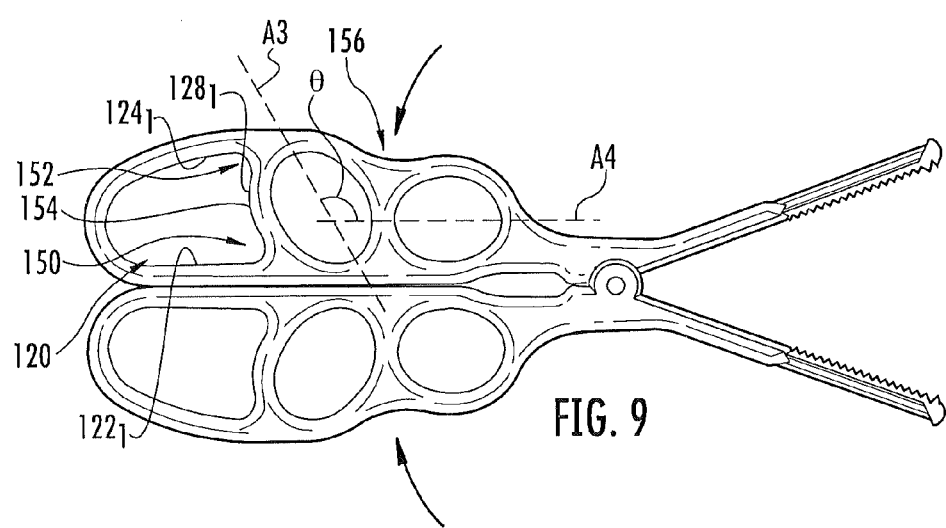
FIG. 9 is a side view of the surgical instrument of FIG. 8 in a second position according to some embodiments.

FIGS. 8 and 9 illustrate a surgical instrument 300 according to other embodiments. The instrument 300 includes first and second pivotally connected members 112, 114. Each member 112, 114 includes a working portion 20 and a pivot portion 24 and the members 112, 114 are pivotally connected at a pivot member 26 as described above in connection with the instruments 1, 10 and 200. The instrument 10 differs from the previously described instruments in the configuration of the handle 116 associated with each member 112, 114.

Each handle 116 includes a first opening 120 defined by an inner wall 122, an outer wall 124, a first end wall 126 at the first end 18 of the member, and a first interior wall 128. Each handle 116 also includes a second opening 130 defined by the inner wall 122, the outer wall 124, a second end wall 132 and a second interior wall 134. Each handle 116 also includes a third opening 140 defined by the inner wall 122, the outer wall 124, the first interior wall 128 and the second interior wall 134.

Thus, the third opening 140 is positioned generally between the first and second openings 120, 130. The second end wall 132 is positioned closer to the pivot portion 24 than is the first end wall 126 and, in some embodiments, the second end wall 132 is positioned adjacent or proximate the pivot portion 24.

The handles 116 are substantially identical and therefore the instrument 300 is reversible and does not require substantial reorientation when grabbed blindly with either hand. The instrument 300 is configured for one-handed operation such that a user's thumb can be received in one of the first, second and third openings 120, 130, 140 of one of the handles 116 and at least one of the user's fingers can be received in the first opening 120, the second opening 130 and/or the third opening 140 of the other one of the handles 116. The user can urge his or her thumb and fingers against the inner surfaces of the walls defining the openings 120, 130, 140 for control during use. The inner surfaces of the walls defining the openings 120, 130, 140 are smooth to prevent abrasions or other injuries during use.

Figure 10:
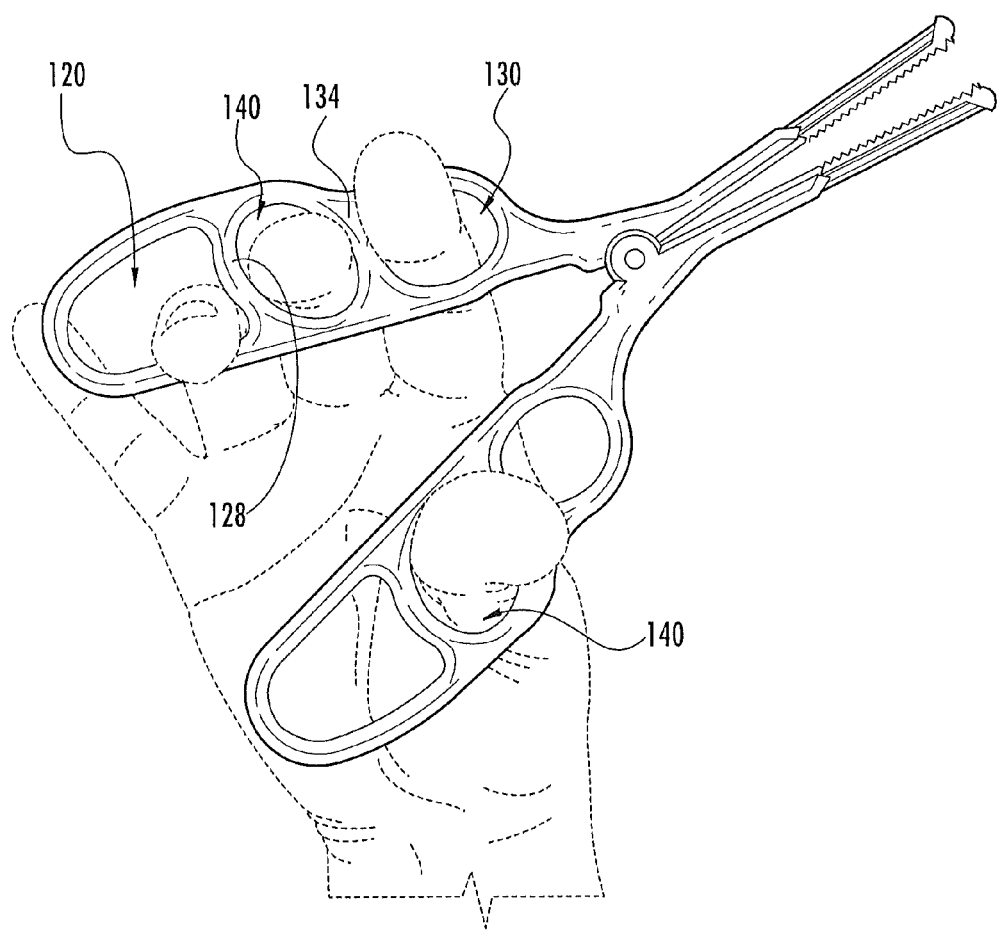
FIG. 10 is a schematic illustration of an exemplary way to grasp and/or manipulate the surgical instrument of FIG. 8.

It will be appreciated that the instrument 300 can be held and manipulated in a variety of ways to provide control as well as accommodate different user preferences and hand sizes. In one exemplary configuration, the user's thumb may be received in the third opening 140 of one of the handles 116. In the other of the handles 116, the user's forefinger may be received in the second opening 130, the user's middle finger may be received in the third opening 140, and the user's ring finger (and possibly the user's little finger) may be received in the first opening 120. This exemplary way of grasping the instrument is illustrated in FIG. 10.

The walls defining the openings 120, 130, 140 may prevent the user's thumb and fingers from slipping out during operation. In addition, at least a portion of the interior walls 128, 134 may serve as one or more "control points" for the user's fingers in the adjacent openings. For example, with the instrument 300 grasped in the above-described manner, the user may urge his or her forefinger against an inner surface 134$_2$ of the interior wall 134 and/or may urge his or her middle finger against an inner surface 134$_3$ of the interior wall 134 to provide greater control. Furthermore, the user may urge his or her middle finger against an inner surface 128$_3$ of the interior wall 128 and/or may urge his or her ring finger against an inner surface 128$_1$ of the interior wall 128 to provide greater control, as described in more detail below.

In the illustrated embodiment, the first opening 120 is elongated and the second and third openings 130, 140 are generally elliptical or oval in shape. It is contemplated that second opening 130 and/or the third opening 140 may be circular or substantially circular in shape. As illustrated in FIGS. 8 and 9, the third opening 140 is slightly elongated relative to the second opening 130. Also as illustrated, the third opening 140 is oriented at an angle relative to the second opening. As shown in FIG. 9, a major axis A3 of the third opening 140 may be oriented at an oblique angle θ to a major axis A4 of the second opening. This configuration allows for a thumb to fit diagonally in the third opening 140 of one of the handles 116 while a smaller finger fits horizontally in the third opening 140 of the other one of the handles 116. Thus, the finger residing in one of the third openings 140 is positioned closer to adjacent fingers positioned in the first opening 120 and/or the second opening 130, which allows for additional control through the above-described control points.

Furthermore, the inner surfaces of the walls defining the first opening 120 may be contoured to provide for additional versatility and contact points. As illustrated in FIG. 9, the inner surface 128$_1$ of first interior wall 128 includes a first rounded portion 150 adjacent an inner surface 122$_1$ of the inner wall 122 and a second rounded portion 152 adjacent an inner surface 124$_1$ of the outer wall 124. The first and second rounded portions 150, 152 are separated by a relatively raised center portion 154 of the inner surface 128$_1$ of first interior wall 128. Thus, the first and second rounded portions 150, 152 may be thought of as "valleys" relative to the raised center portion 154.

Users of various hand sizes may wedge their finger or thumb in the first and second rounded portions or valleys 150, 152. For example, the user may wedge his or her finger/thumb in the first rounded portion 150 while closing the handles 116 and in the second rounded portion 152 while opening the handles. This provides for additional control through the control points associated with the interior wall 128.

Some of the above-described features are illustrated in FIG. 10. As shown, the user's thumb can fit diagonally in the third opening 140 of one of the handles. The user's forefinger can fit in the second opening 130 of the other of the handles, and the user's middle finger can fit horizontally in the adjacent third opening 140. It can be seen that this configuration allows at least a portion of the interior wall 134 to serve as a control point for the adjacent fingers. Moreover, the user's ring finger can be positioned in the first opening 120, and in particular can wedge in the rounded portion 154 (FIG. 9) adjacent the interior wall 128 to provide additional control. The user can optionally position his or her little finger in the first opening 120. It is stressed that this is just one exemplary way to grasp and manipulate the instrument, and that the openings 120, 130, 140 allow for the user to grasp and manipulate the instrument in many different ways so as to provide the most comfort, controllability and/or leverage based on the user's hand size and preference.

Referring back to FIG. 9, the outer surfaces of each of the outer walls 124 are smooth and may also receive a thumb or one or more fingers of the user. A user may find that placing his or her thumb or at least one finger on one or both of these outer surfaces may allow for greater leverage when closing the handles, for example. In the illustrated embodiment, the outer surfaces of the outer walls 124 includes a valley 156 located between the second and third openings 130, 140. The valley 156 may provide another contact point for the user's thumb or finger in the above-described manner of use.

Thus, it will be appreciated that the openings 120, 130, 140 of the handles 116 allow users to grasp the instrument 300 in a variety of ways to provide the desired comfort and controllability and/or to provide the leverage needed in a particular application. Thumbs and fingers of varying sizes may be placed in any openings 120, 130, 140 or even on the outer surface of the outer walls 124.

It is also noted that a user may grasp the instrument 300 with one or more fingers on each of the working portions 20 adjacent the pivot portions 24, on each of the pivot portions 24 and/or against an outer surface of the second end wall 132, with the user's thumb and/or palm wedged between the handles 116. This manner of grasping the instrument may be useful during insertion of the working portions 20 into an opening by helping to ensure that the working portions 20 remain closed during insertion. The user may then reorient his or her hand to grasp the handles 116 such as in the manner described above to perform the steps of enlarging the opening, grasping an object and/or extracting the object. As described in more detail below, the handles may also be biased in an open position to help ensure the working portions remain closed during insertion.

Figure 11A:
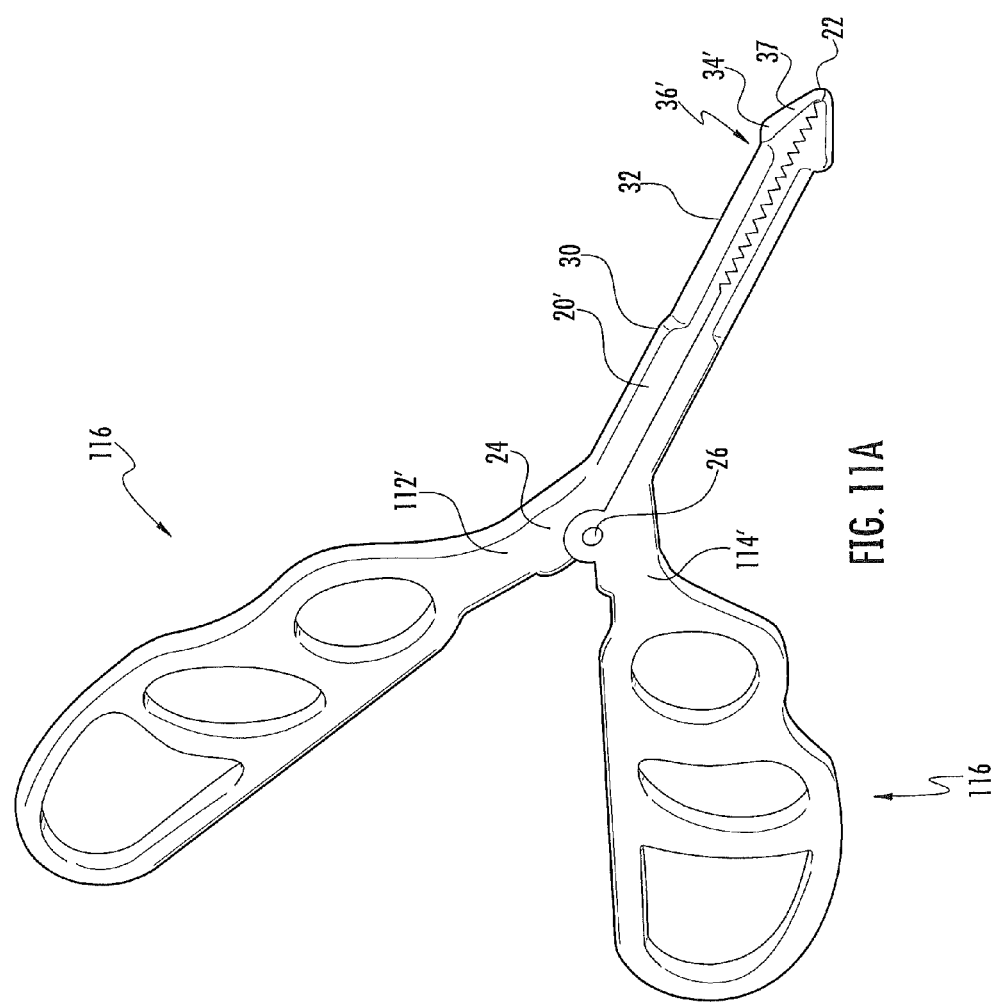
FIG. 11A is a side perspective view of a surgical instrument in a first position according to some other embodiments.
Figure 11B:
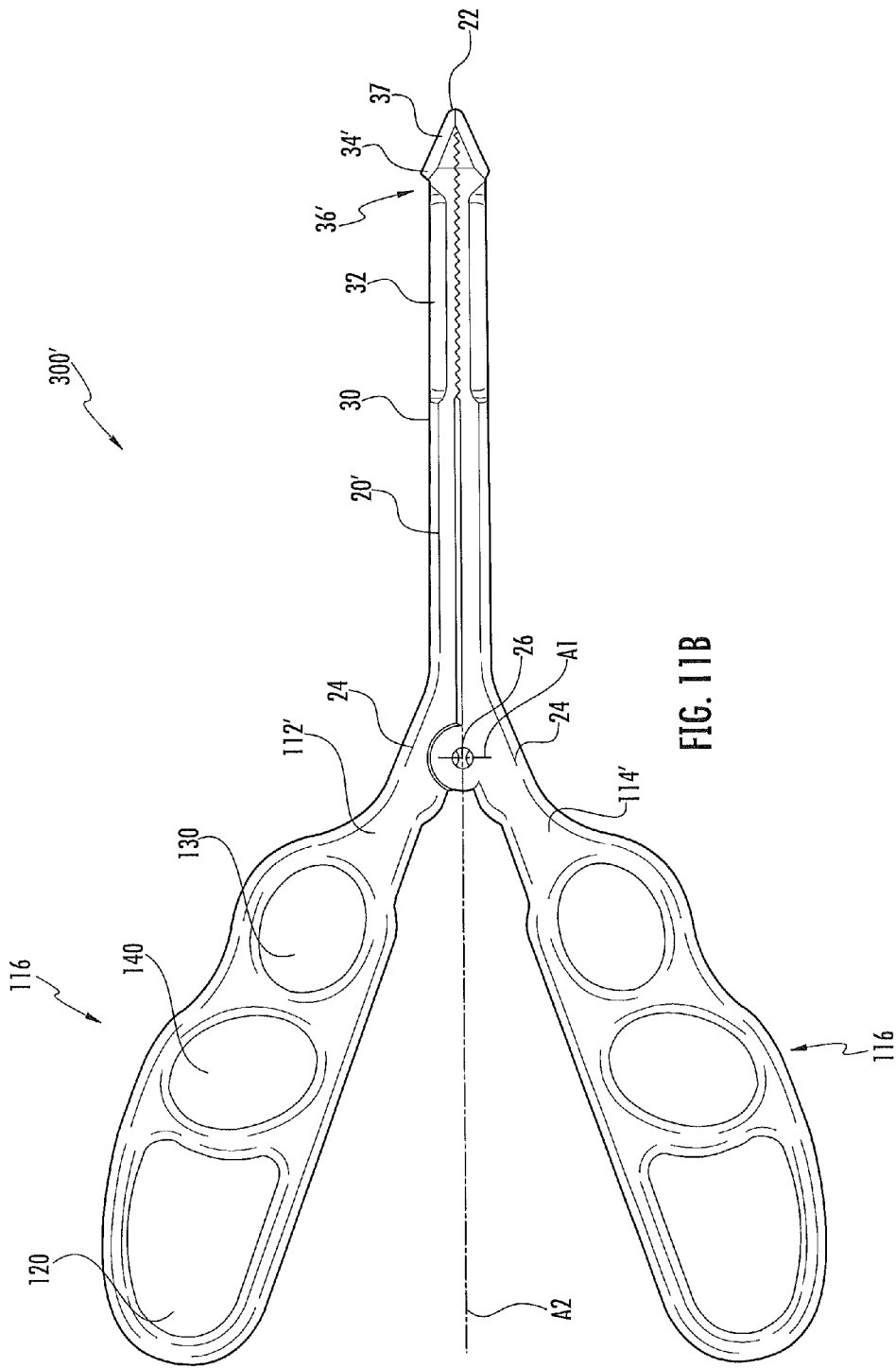
FIG. 11B is a side view of the surgical instrument of FIG. 11A in the first position.
Figure 11C:
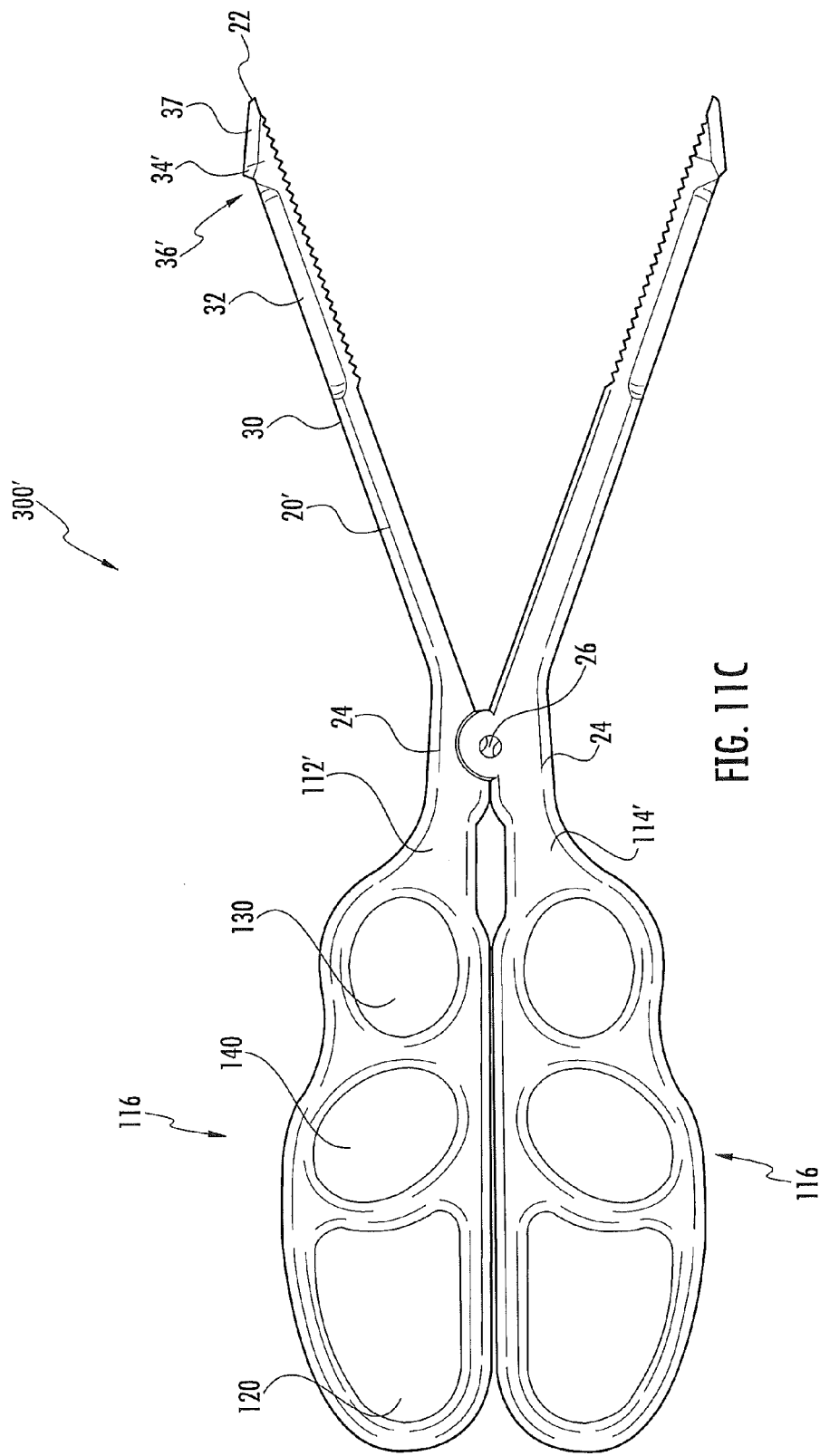
FIG. 11C is a side view of the surgical instrument of FIG. 11A in a second position according to some embodiments.

FIGS. 11A-11C illustrate a surgical instrument 300' according to other embodiments. Each member 112', 114' includes a handle 116 as described above in connection with the instrument 300. Each member 112', 114' also includes a pivot portion 24 and the members 112', 114' are pivotally connected at a pivot member 26 as described above in connection with the previously described instruments. The instrument 300' differs from the previously described instruments in the following respects.

Each member 112', 114' includes a working portion 20' that is slightly different than the working portions 20 described above. Each working portion 20' has a wedge 32 as described above. Adjacent each wedge 32 is an outwardly extending lip 34', similar to the lip 34 described above. Each wedge 32 and lip 34' defines a valley 36' therebetween on the outer surface 30 of the working portion 20, similar to the valley 36 described above.

As illustrated, each working portion 20' includes a portion 37 that tapers inwardly from the lip 34' to the second end 22 of a respective member 112', 114'. That is, the tapered portions 37 taper inwardly toward the axis A2 that is normal to the axis A1 defined by the pivot portion 26 and extends between the working portions 20' and/or the handles 116 (FIG. 11B). The tapered portions 37 may also taper inwardly toward or along the axis A1 from the lip 34' to the second end 22 of a respective member 112', 114'. When the tapered portions 37 taper inwardly in both the A2 and the A1 axes, a conical or pseudo-conical end is formed when the working portions 20' are closed. In some embodiments, the tapered portions 37 may taper inwardly in both directions along a width that extends along an axis that is parallel to the axis A1 (i.e., an axis that is normal to the axis A2 and extends between the tapered portions 37). In these configurations, a conical or pseudo-conical end is formed when the working portions 20' are closed. The tapered portions 37 may also be rounded along at least a portion of a width that extends parallel to the axis A1. As shown in FIGS. 11A and 11B, the second ends 22 of the first and second members 112', 114' are shaped such that, when the handles 116 are in the open position, the adjacent second ends 22 define a blunt tip. In this regard, the area defined by the portions 37 resembles an arrowhead when the handles are in the closed position. The second ends 22 of the first and second members 112', 114' may be flat or rounded in various embodiments to form the blunt tip.

This configuration can provide several advantages. First, the tapered portions 37 allow the working portions 20' to be more easily inserted into in a variety of differently sized openings. For example, the tapered portions 37 may allow the working portions 20' to be inserted into a relatively small trochar port site (e.g., 5 mm diameter) such that the opening may be enlarged and an organ or a portion thereof may be extracted from the enlarged opening. Further, the end portions that define the blunt tip provide safety for both the patient and the surgeon. Regarding the patient, when the working portions 20' are inserted into an opening, the blunt tip is less likely to puncture the interior vena cava or an organ as compared to a sharper tip. The blunt tip is also less likely to injure or "stick" the surgeon or other user during handling. Finally, the lips 34' and valleys 36' can provide locating and tactile feedback advantages as described above in reference to the lips 34 and valleys 36.

Figure 12A:
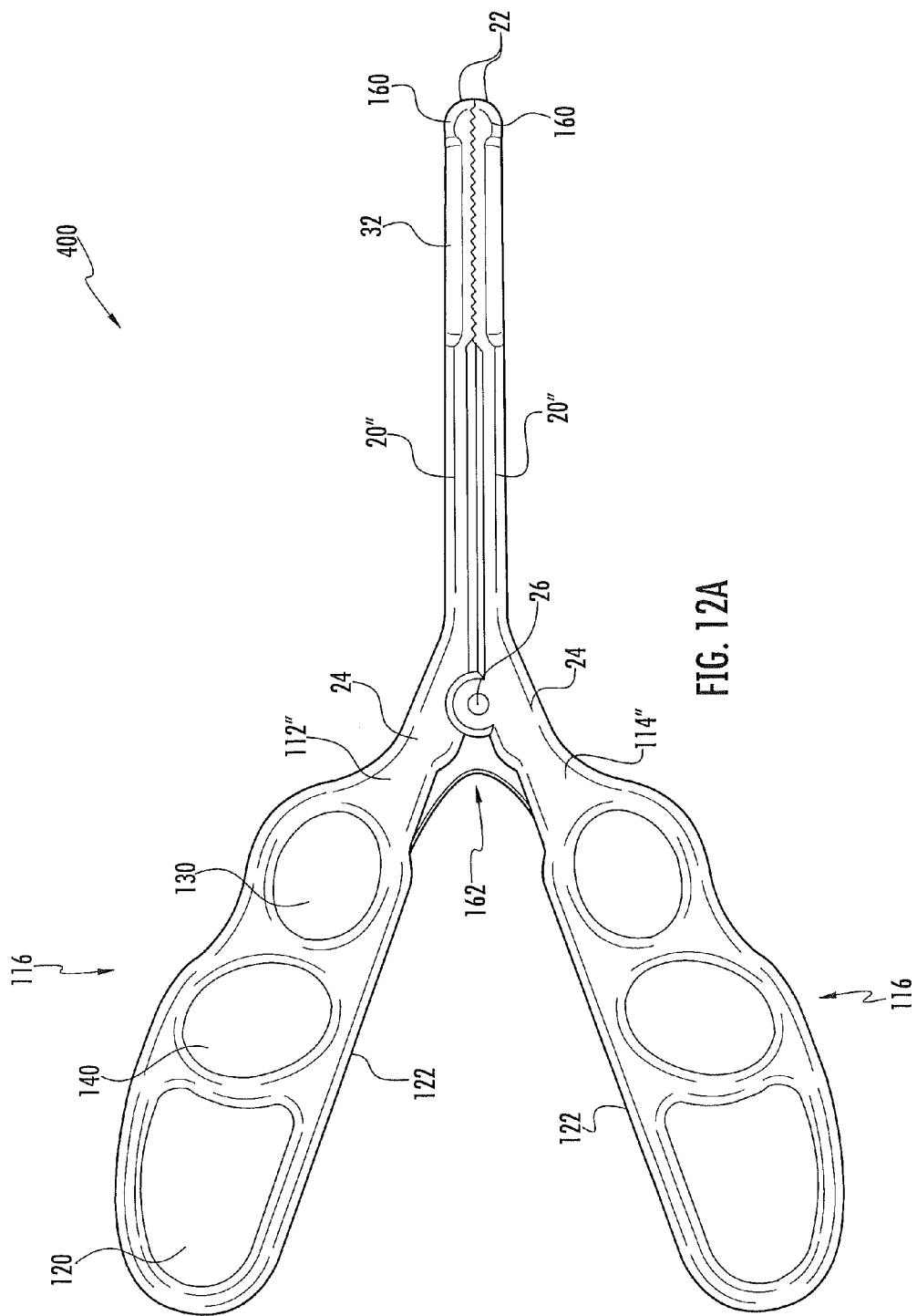
FIG. 12A is a side view of a surgical instrument in a first position according to some embodiments.
Figure 12B:
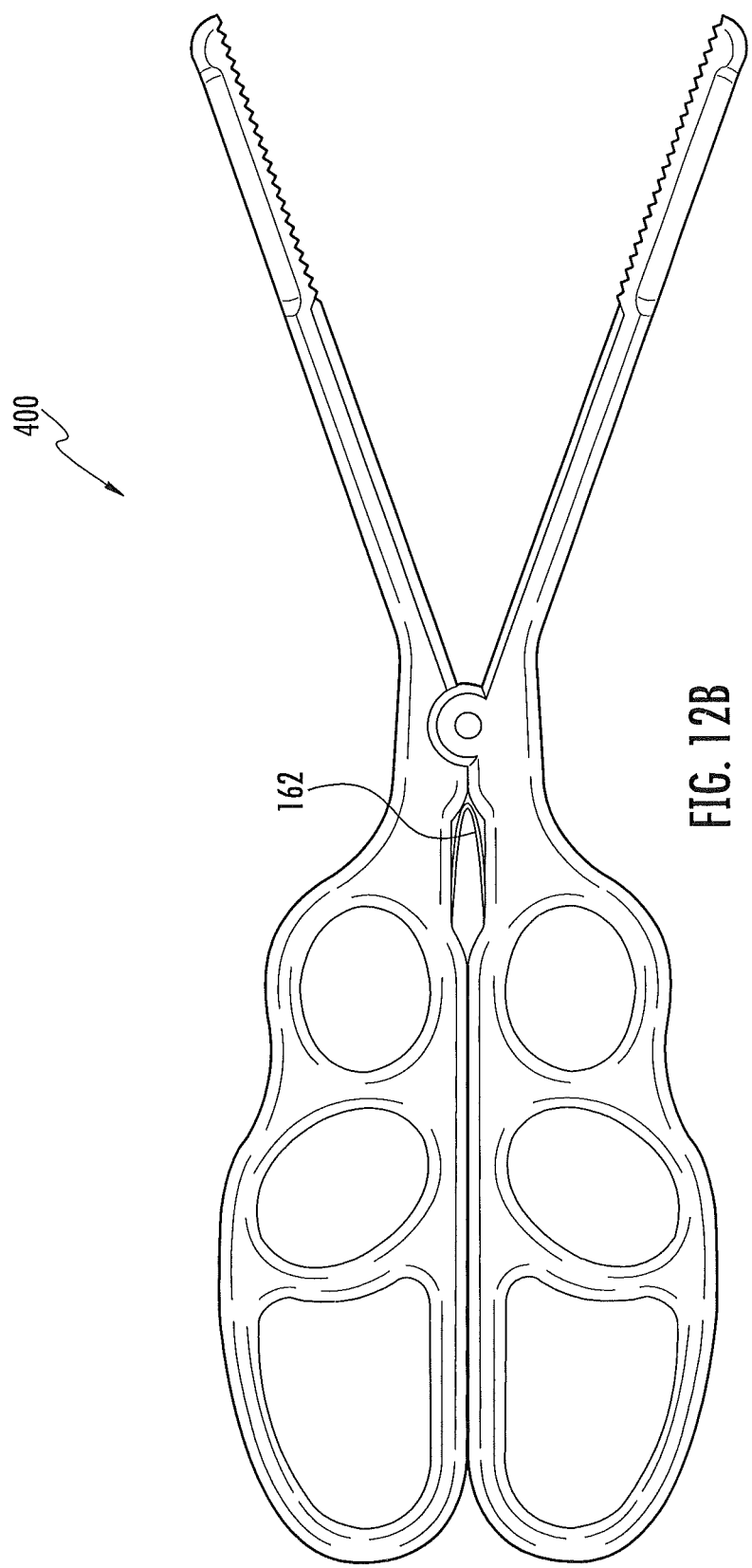
FIG. 12B is a side view of the surgical instrument of FIG. 12A in a second position according to some embodiments.

FIGS. 12A and 12B illustrate a surgical instrument 400 according to other embodiments. The instrument 400 includes first and second pivotally connected members 112", 114". Each member 112", 114" includes a handle 116 as described above in connection with the instrument 300. Each member 112", 114" also includes a pivot portion 24 and the members 112", 114" are pivotally connected at a pivot member 26 as described above in connection with the previously described instruments. The instrument 400 differs from the previously described instruments in the following respects.

Each member 112', 114' includes a working portion 20''' that is slightly different than the working portions 20 and 20' described above. Each working portion 20''' has a wedge 32 as described above. However, adjacent the wedge 32, each working portion 20''' has a rounded end portion 160 terminating at the second end 22 of the member. Thus, the instrument 400 differs from the previously described instruments by excluding the lips at the ends of the working portions. This configuration may provide for easier insertion of the working ends 20''' into an opening that is to be enlarged and/or through which an object is to be extracted (FIG. 4).

The instrument 400 also includes a biasing member 162 to bias the handles in the first or open position (FIG. 12A). The biasing member 162 may be any biasing member known to those of skill in the art, such as a spring. As illustrated, the biasing member 162 attaches to the handle inner walls 122 adjacent the pivot portions 24. However, other arrangements are contemplated; as just one example, the biasing member may be integrated with the pivot member 26.

The biasing member 162 may be useful to bias the instrument 400 in a "default position" in which the working portions 20''' are adjacent one another. It is contemplated that the instrument is most likely to be inserted into an opening such as a trochar site in this position prior to enlarging the opening and/or grasping and extracting an organ. As described above and set forth in additional detail below, the handles may be moved toward a second or closed position (FIG. 12B) in order to enlarge the opening. The biasing member 162 may provide greater control in this operation and prevent the opening from being enlarged too much or too rapidly. Moreover, after an organ has been grasped, the biasing member 162 may be useful in ensuring that the organ remains tightly grasped as it is extracted from the opening. Of course, a biasing member such as the biasing member 162 may be employed in any of the surgical instruments described above.

Figure 13:
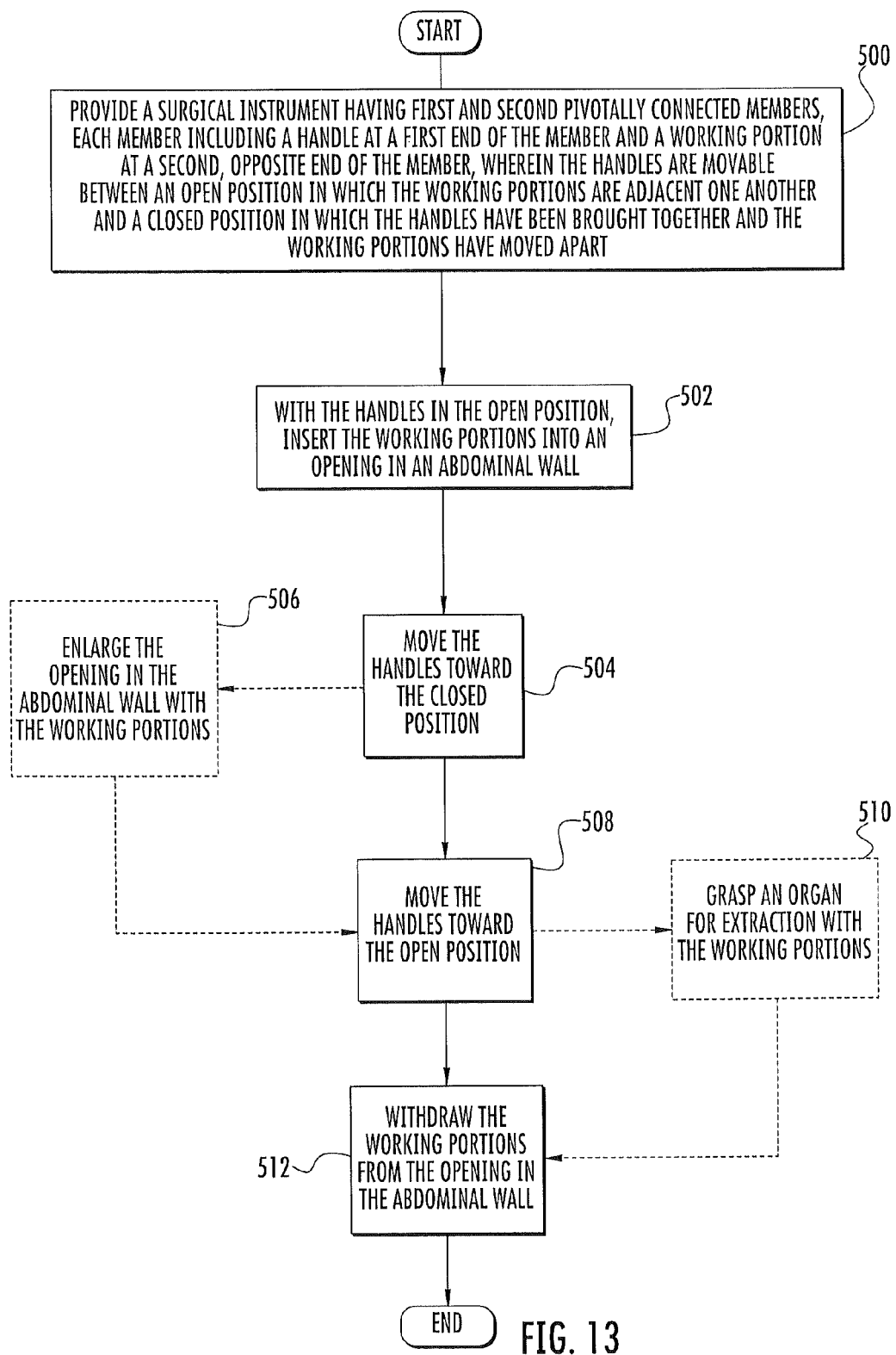
FIG. 13 is a flowchart illustrating exemplary operations performed by the surgical instruments of FIGS. 1-12.

Exemplary operations associated with minimally invasive surgery, such as laparoscopic surgery, are illustrated in FIG. 13. A surgical instrument, such as any of the surgical instruments described above, is provided (Block 500). The instrument generally has first and second pivotally connected members, with each member including a handle at a first end of the member and a working portion at a second, opposite end of the member. The handles are movable between an open position in which the working portions are adjacent one another and a closed position in which the handles have been brought together and the working portions have moved apart.

With the handles in the open position, the closed working portions are inserted into an opening in an abdominal wall (Block 502). An exemplary abdominal wall opening is the trochar site opening illustrated in FIG. 4. The handles are then moved toward the closed position (Block 504). Optionally, the abdominal wall opening is enlarged by the working portions (Block 506) due to the handles being moved toward the closed position.

The handles are then moved toward the open position (Block 508). The handles may be moved toward the open position manually or a biasing member may urge the handles toward the open position. Optionally, an object such as an organ is grasped with the working portions (Block 510) due to the handles being moved toward the open position. The working portions are then withdrawn from the abdominal opening (Block 512). If the organ was grasped (Block 510), then this step includes withdrawing the working portion and the grasped organ together.

The surgical instruments described above are typically made of a rigid material. At least a portion of the surgical instruments, such as the working portions, are typically made of a metal or metal alloy that is corrosion resistant, such as stainless steel. It is contemplated that at least the handles may be made of a non-metallic material such as a relatively strong polymeric material.

The working portions 20 (e.g., FIGS. 1 and 2), 20' (FIGS. 11A-C) and 20" (FIGS. 12A and 12B) may have a variable length depending on body habitus and/or the size and type of organ to be extracted. Also, the working portions may have a width, extending parallel to the axis defined by the pivot member (e.g., axis A1 shown in FIGS. 2 and 11B) such that the working portions are configured to be inserted into relative small openings formed in the abdomen or chest. In some embodiments, the working portions have a width of about 5 mm or less to accommodate insertion into relatively small trochar site openings.

Figure 14A:
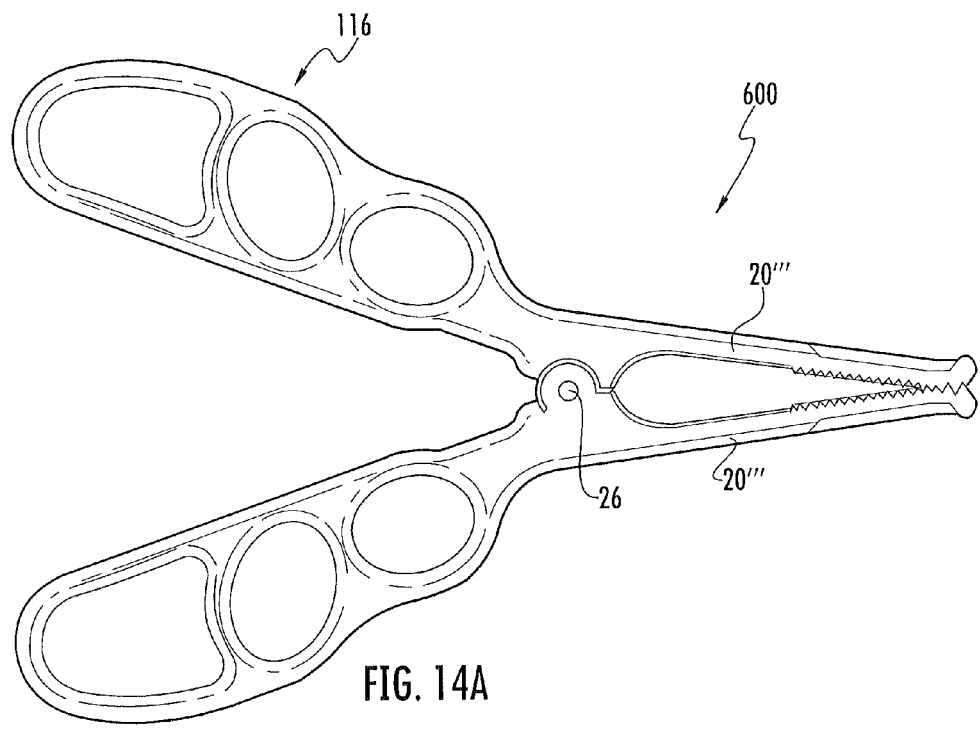
FIG. 14A is a side view of a surgical instrument in a first position according to some other embodiments.
Figure 14B:
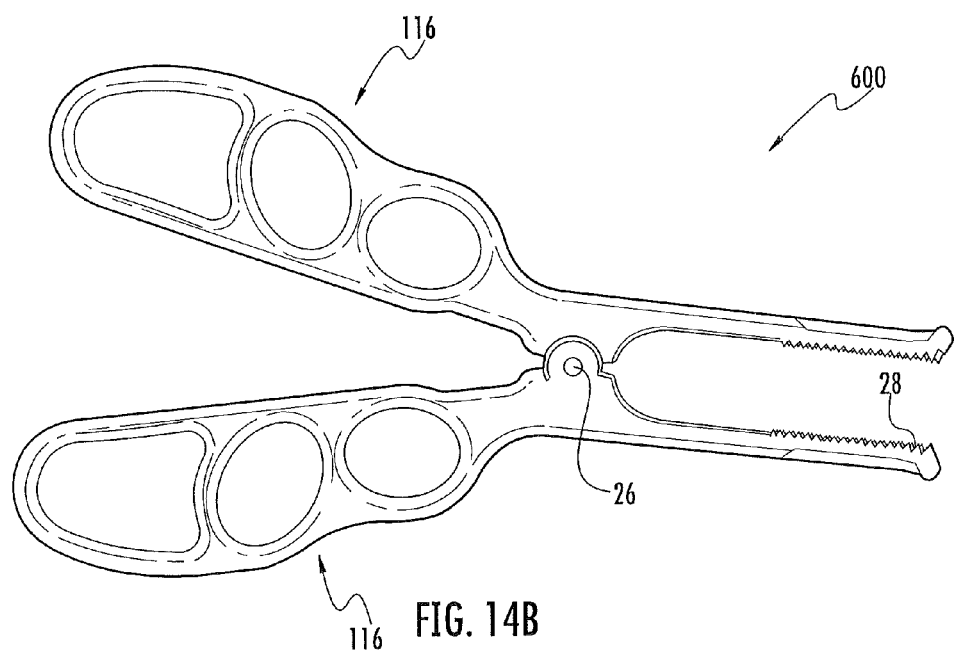
FIG. 14B is a side view of the surgical instrument of FIG. 14A in a second position according to some embodiments.

It is contemplated that, in some embodiments, the working portions may be curved or bent at an angle or spaced apart adjacent the pivots portions. For example, referring to FIGS. 14A and 14B, the working portions 20''' are bent or curved upward near the pivot member 26. In this configuration, the working portions 20' are spaced apart when the handles 116 are moved toward the second or "closed" position (FIG. 14B). This may allow the teeth 28 of the working portions 20''' to be more parallel to the object being grasped and ensure a firm grip during extraction.

Although not illustrated, in some embodiments, the working portions may be curved or bent sideways such that the instrument can be used flat or from the side. In this sense, the handles are out of the direct line of sight during use.

It is important to note that the handles described above are thought to be unique in their comfort, ergonomics, versatility, and ability to provide precise control. As such, it is contemplated that the handles, and particularly the handles 16" described in connection with instrument 200 (FIG. 6) and the handles 116 described in connection with instruments 300 (FIGS. 8 and 9), 300' (FIGS. 11A-C) and 400 (FIGS. 12A-B), can be effectively employed in a variety of instruments and tools, and not simply the specialized surgical instruments described above. To list just a few exemplary applications, the handles may be employed with common tools such as scissors, hedge clippers, pliers, and wrenches as well as other surgical instruments.

Figure 15:
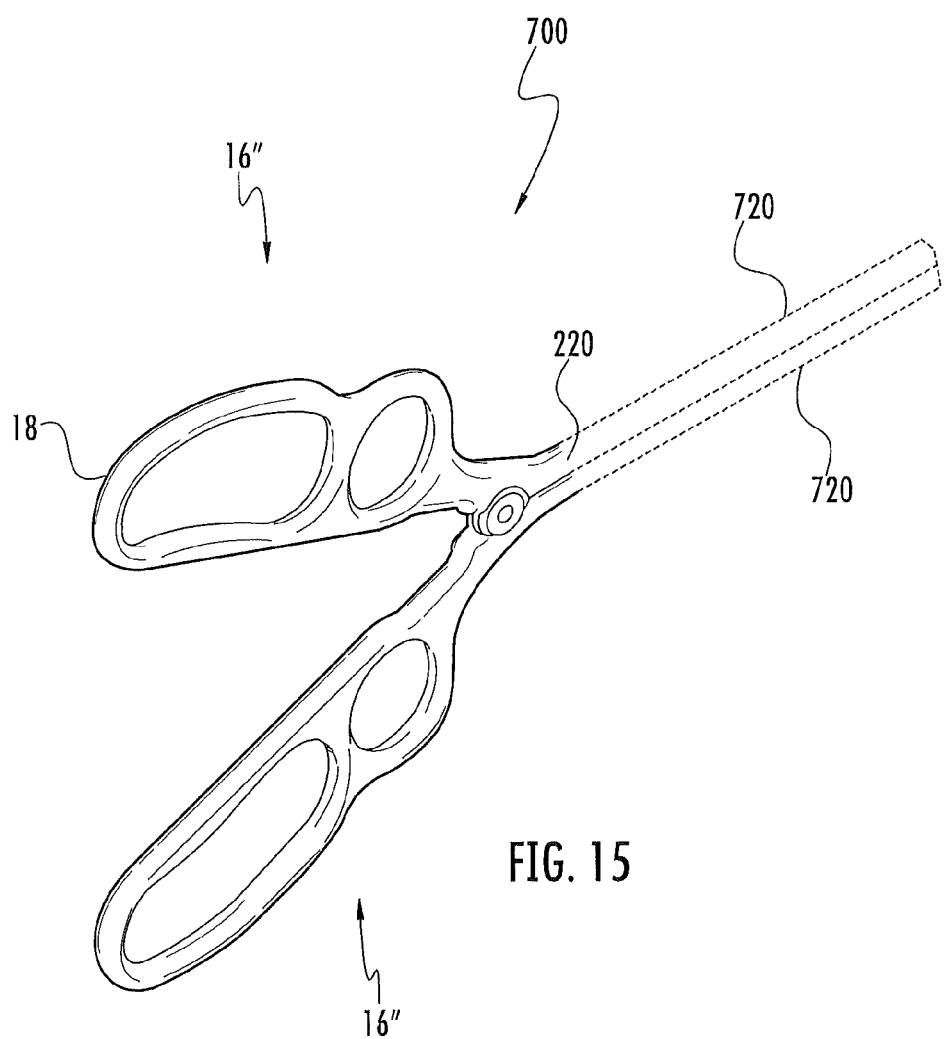
FIG. 15 is a perspective view of a handle system for use with tools according to some embodiments.
Figure 16:
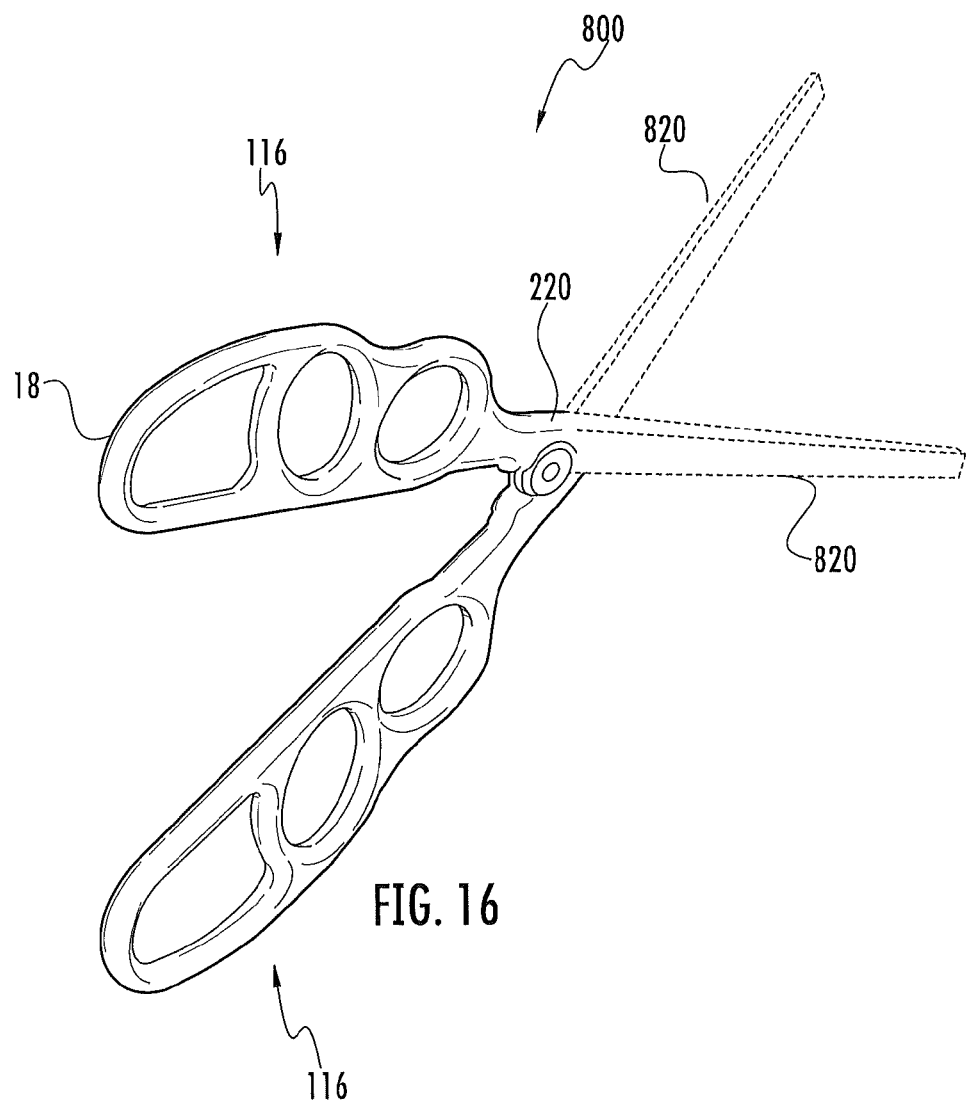
FIG. 16 is a perspective view of a handle system for use with tools according to some other embodiments.

Turning to FIG. 15, the tool 700 includes a pair of pivotally connected handles 16". Each handle 16" includes a first end 18 and a second end 220. A working portion 720 can be either integrated with or attached/connected to each handle 16" at the second end 220. Similarly, referring to FIG. 16, the tool 800 includes a pair of pivotally connected handles 116. Each handle 116 includes a first end 18 and a second end 220. A working portion 720 can be either integrated with or attached/connected to each handle 16" at the second end 220. The tools 700, 800 can be configured to have either a "reverse-scissors" action (FIG. 15) or a scissors-like action (FIG. 16), as defined above.

Many alterations and modifications may be made by those having ordinary skill in the art, given the benefit of present disclosure, without departing from the spirit and scope of the invention. Therefore, it must be understood that the illustrated embodiments have been set forth only for the purposes of example, and that it should not be taken as limiting the invention as defined by the following claims. The following claims, therefore, are to be read to include not only the combination of elements which are literally set forth but all equivalent elements for performing substantially the same function in substantially the same way to obtain substantially the same result. The claims are thus to be understood to include what is specifically illustrated and described above, what is conceptually equivalent, and also what incorporates the essential idea of the invention.

That which is claimed is:

1. A surgical instrument, comprising:
    first and second members, each member including a handle adjacent a first end of the member, a working portion having an inner surface and an outer surface and extending from a second, opposite end of the member, and a pivot portion located between the handle and the working portion;
    wherein the first and second members are pivotally connected at the pivot portions about a pivot axis such that the handles are movable between an open position in which the handles are spaced apart and the working portions are adjacent one another and a closed position in which the handles have been brought together and the working portions are spaced apart;
    wherein each working portion includes an outwardly tapering wedge and an outwardly extending lip adjacent the wedge, wherein the wedge and the lip define a valley therebetween on the working portion outer surface.

2. The surgical instrument of claim 1, wherein each working portion includes a tapered portion that tapers inwardly from the lip to the second end of a respective first and second member.

3. The surgical instrument of claim 2, wherein the second end of each of the first and second members is shaped such that, when the handles are in the open position, the adjacent second ends of the first and second members define a blunt tip.

4. The surgical instrument of claim 1, wherein the second end of the first and second members is rounded.

5. The surgical instrument of claim 1, wherein at least a portion of each working portion inner surface comprises a plurality of teeth.

6. The surgical instrument of claim 1, further comprising a biasing member positioned between the handles and configured to bias the handles toward the open position.

7. The surgical instrument of claim 1, wherein the handles are substantially symmetrical about an axis that is normal to the pivot axis and extends between the working portions.

8. The surgical instrument of claim 7, wherein at least a major portion of a length of the handle of each member is contoured inwardly from the first end of the member to the pivot portion of the member.

9. The surgical instrument of claim 7, wherein the handle of each member includes at least one opening defined by an inner wall, an outer wall, a first end wall at the first end of the member and a second end wall located adjacent the pivot portion of the member.

10. The surgical instrument of claim 9, wherein the handle of each member includes a first opening defined by the inner wall, the outer wall, the first end wall, and an interior wall and a second opening defined by the inner wall, the outer wall, the second end wall, and the interior wall, wherein the first opening is elongated and the second opening is generally oval and separated from the first opening by the interior wall.

11. The surgical instrument of claim 9, wherein the handle of each member includes:
a first opening defined by the inner wall, the outer wall, the first end wall, and a first interior wall;
a second opening defined by the inner wall, the outer wall, the second end wall, and a second interior wall; and
a third opening defined by the inner wall, the outer wall, and the first and second interior walls, the third opening located between the first and second openings of the handle;
wherein the first opening is elongated and the second and third openings are generally oval.

12. The surgical instrument of claim 11, wherein the third opening is elongated relative to the second opening and oriented at an oblique angle relative to a major axis of the second opening.

13. The surgical instrument of claim 12, wherein the first opening of each handle is contoured such that the first interior wall has a first rounded portion adjacent the inner wall and a second rounded portion adjacent the outer wall, the first and second rounded portions separated by relatively raised center portion.

14. The surgical instrument of claim 12, wherein the outer wall of each member is contoured such that the outer wall includes a valley.

15. A handle system for use with a tool, the handle system comprising:
first and second elongated handles, each handle extending from a first end to a second opposite end, each handle including an inner wall, an outer wall, a first end wall at the first end of the handle and extending between the inner wall and the outer wall, and a second end wall located proximate the second end of the handle and extending between the inner wall and the outer wall, wherein the handles are pivotally connected at the handle second ends such that the handles are pivotable between an open position wherein the inner walls are spaced apart and a closed position wherein the inner walls are adjacent one another, wherein each handle comprises:
a first elongated opening defined by the first end wall, the inner wall, the outer wall and an interior wall located between the first and second end walls and extending between the inner and outer walls; and
a second generally oval opening defined by the second end wall, the inner wall, the outer wall and the interior wall.

16. The handle system of claim 15, wherein each handle includes first and second interior walls that each extend between the inner and outer walls and a third generally oval opening, and wherein:
the first elongated opening is defined by the first end wall, the inner wall, the outer wall and first interior wall;
the second generally oval opening is defined by the second end wall, the inner wall, the outer wall and the second interior wall; and
the third generally oval opening is located between the first and second openings and is defined by the inner wall, the outer wall, and the first and second interior walls.

17. The handle system of claim 16, wherein the third opening is elongated relative to the second opening and oriented at an oblique angle relative to a major axis of the second opening.

18. The handle system of claim 17, wherein the first opening of each handle is contoured such that the first interior wall has a first rounded portion adjacent the inner wall and a second rounded portion adjacent the outer wall, the first and second rounded portions separated by relatively raised center portion.

19. The handle system of claim 17, wherein an outer surface of each handle outer wall is contoured inwardly from the third opening to the second opening.

20. A handle system for use with a tool, the handle system comprising:
first and second elongated handles, each handle extending from a first end to a second opposite end adapted to receive a working end portion, wherein the handles are pivotally connected proximate their second ends and are pivotable about a pivot axis, each handle comprising:
an inner wall, an outer wall, a first end wall located at the first end of the handle and extending between the inner and the outer wall, a first interior wall located closer to the second end of the handle than the first end wall and extending between the inner and the outer wall, a second interior wall located closer to the second end of the handle than the first interior wall and extending between the inner and the outer wall, and a second end wall located closer to the second end of the handle than the second interior wall and extending between the inner and the outer wall;
a first elongated opening defined by the first end wall, the inner wall, the outer wall and the first interior wall;
a second generally elliptical opening defined by the second end wall, the inner wall, the outer wall and the second interior wall; and
a third generally elliptical opening located between the first and second openings and defined by the inner wall, the outer wall, and the first and second interior walls.

21. The handle system of claim 20 in combination with a pair of working end portions, one each extending from a respective second end of the first and second handles, wherein the handles are configured such that as the handles are moved apart the working portions come together and as the handles are brought together the working portions move apart.

22. The handle system of claim 20, wherein the third opening is elongated relative to the second opening and oriented at an oblique angle relative to a major axis of the second opening.

23. The handle system of claim 20, wherein the first opening of each handle is contoured such that an inner surface of the first interior wall has a first rounded portion adjacent the inner wall and a second rounded portion adjacent the outer wall, the first and second rounded portions separated by relatively raised center portion of the inner surface of the first interior wall.

24. The handle system of claim 20, wherein each handle outer wall is contoured such that an outer surface of the outer wall includes a valley.

25. The handle system of claim 20, wherein the first and second handles are substantially symmetrical about an axis that is normal to the pivot axis and extends between the handles.

26. The handle system of claim 20 in combination with a pair of working end portions, one each extending from a respective second end of the first and second handles, wherein the handles are configured such that as the handles are moved apart the working portions move apart and as the handles are brought together the working portions come together.

27. A method of performing laparoscopic surgery, comprising:
    providing a tool having first and second pivotally connected elongated members, each member including a handle extending from a first end of the member and a working portion extending from a second, opposite end of the member, wherein the handles are movable between an open position in which the working portions are adjacent one another to a closed position in which the handles have been brought together and the working portions have moved apart;
    with the handles in the open position, inserting the working portions in an opening in an abdominal wall; then
    moving the handles toward the closed position; then
    moving the handles toward the open position;
    grasping an organ for extraction with the working portions during the step of moving the handles toward the open position; and then
    withdrawing the working portions from the opening in the abdominal wall including withdrawing the working portions and the grasped object from the opening.

28. The method of claim 27, further comprising enlarging the opening of the abdominal wall with the working portions during the step of moving the handles toward the closed position.

\* \* \* \* \*